US008481580B2

(12) United States Patent
Macdonald et al.

(10) Patent No.: US 8,481,580 B2
(45) Date of Patent: Jul. 9, 2013

(54) LISOFYLLINE ANALOGS AND METHODS FOR USE

(75) Inventors: Timothy L. Macdonald, Charlottesville, VA (US); Jerry L. Nadler, Charlottesville, VA (US); Peng Cui, Los Angeles, CA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1082 days.

(21) Appl. No.: 12/036,646

(22) Filed: Feb. 25, 2008

(65) Prior Publication Data

US 2008/0146544 A1    Jun. 19, 2008

Related U.S. Application Data

(63) Continuation of application No. PCT/US2006/033777, filed on Aug. 29, 2006.

(60) Provisional application No. 60/712,114, filed on Aug. 29, 2005.

(51) Int. Cl.
| | |
|---|---|
| *A61P 9/10* | (2006.01) |
| *A61P 19/02* | (2006.01) |
| *A61P 25/28* | (2006.01) |
| *A61K 31/41* | (2006.01) |
| *C07D 249/12* | (2006.01) |

(52) U.S. Cl.
USPC ..................... 514/384; 548/263.6

(58) Field of Classification Search
USPC ........................ 514/384; 548/263.6
See application file for complete search history.

(56) References Cited

U.S. PATENT DOCUMENTS

| | | | |
|---|---|---|---|
| 2,748,125 A | 5/1956 | Hofmann | |
| 4,160,452 A | 7/1979 | Theeuwes | |
| 4,256,108 A | 3/1981 | Theeuwes | |
| 4,265,874 A | 5/1981 | Bonsen et al. | |
| 4,861,778 A | 8/1989 | Hall et al. | |
| 4,866,058 A * | 9/1989 | Izydore et al. | 514/241 |
| 4,938,949 A | 7/1990 | Borch et al. | |
| 5,192,761 A * | 3/1993 | Izydore et al. | 514/241 |
| 5,719,155 A | 2/1998 | Cho et al. | |
| 6,316,458 B1 | 11/2001 | Nadler | |
| 2004/0048865 A1 | 3/2004 | Purandare | |
| 2010/0105690 A1 | 4/2010 | Macdonald et al. | |

FOREIGN PATENT DOCUMENTS

| | | |
|---|---|---|
| BE | 490069 | 7/1949 |
| WO | WO 99/36073 A | 7/1999 |
| WO | WO 00/61583 | 10/2000 |
| WO | WO 02/068421 A2 | 9/2002 |
| WO | WO 2008/108842 A1 | 9/2008 |

OTHER PUBLICATIONS

Z. D. Yang, M. Chen, R. Wu, M. McDuffie, J. L. Nadler, *Diabetologia*, 2002, 45, 1307-1314.

M. Chen, Z. D. Yang, R. Wu, J. L. Nadler, *Endocrinology*, 2002, 143(6), 2341-2348.
J. D. Hepworth. *Org. Synth.* 5, 27-29, 1925.
R. Calabretta, C. Giordano, C. Gallina, V. Morea, V. Consalvi and R. Scandurra. *Eur. J. Med. Chem.* 1995, 30, 931-941.
S. Horrobin. *J. Chem. Soc.* 1963, 4130-4145.
S. H. Kim, D. G. Bartholomew, and L. B. Allen. *J. Med. Chem.* 1978, 21(9), 883-888.
V. Cere, C. Mazzini, C. Paolucci, S. Pollicino and A. Fava *J. Org. Chem.*, 1993, 58, 4567-4571.
C. Paolucci, S. Pollicino and A. Fava *J. Org. Chem.*, 1995, 60, 169-175.
F. Sato, Y. Tomuro, H. Ishikawa and M. Sato. *Chem. Lett.* 1980, 99-102.
G. Cerichelli, C. Grande, L. Luchetti and G. Mancini *J. Org. Chem.*, 1991, 56, 3025- 3030.
N. Haider, E. Mavrokordatou and A. Steinwender. *Syn. Comm.* 1999, 29(9), 1577-1584.
Cui et al., "Synthesis and biological evaluation of lisofylline (LSF) analogs as a potential treatment for Type 1 diabetes", Bioorganic & Meoicinal Chemistry Letters, Oxforo, GB, vol. 16, No. 13, Jul. 1, 2006, pp. 3401-3405.
Yang, Z. et al., "Lisofylline: a potential lead for the treatment of diabetes", Biochemical Pharmacology, Pergamon, Oxford, GB, vol. 69, No. 1, Jan. 1, 2005, pp. 1-5.
Rybczynski, Philip J. et al., "Benzoxazinones as PPAR.gamma. Agonists. 2. SAR of the Amide Substituent and In Vivo Results in a Type 2 Diabetes Model", Journal of Medicinal Chemistry, 47(1), p. 196-209, 2004.
Keinan E. et al., "Natural ozone scavenger prevents asthma in sensitized rats", Bioorganic & Medicinal Chemistry, Elsevier Science Ltd, GB, vol. 13, No. 2, Jan. 17, 2005 , pp. 557-562.
International Search Report and Written Opinion of PCT International Application No. PCT/US2006/033777 dated Mar. 29, 2007.
Beilstein Institut Zur Forderung Der Wissenschaften, Frankfurt-Main- DE; Database Accession No. BRN 153940 & Istanbul Univ. Fen. Fak. Mecm. Seri A, 13:127 (1948).
Beilstein Institut Zur Forderung Der Wissenschaften, Frankfurt-Main- DE; Database Accession No. BRN 644148 & Hayashi et al., 82:584-588 (1962).
Beilstein Institut Zur Forderung Der Wissenschaften, Frankfurt-Main- DE; Database Accession No. BRN 159592 & Ikeda et al., 88:521-526 (1968).
Beilstein Institut Zur Forderung Der Wissenschaften, Frankfurt-Main- DE; Database Accession No. BRN 646641 & Ikeda et al., 88:521-526 (1968).
Butner et al., "Anti-inflammatory activity of 2,3-dihydrophthalazine-1,4-diones in CF1 mice," Internat. J. Tissue Reactions 18(2/3):47-55 (1996).
Buu-Hoi et al., "Sur l'alkylation de la phthalylhydrazine (phthalaz-1,4-dione)," Recueil des Travaux Chimiques des Pays-Bas et de la Belgique 70:1099-1104 (1951).

(Continued)

*Primary Examiner* — Brenda Coleman

(74) *Attorney, Agent, or Firm* — J.A. Lindeman & Co., PLLC

(57) ABSTRACT

The present invention provides analogs of a Lysofylline (LSF), and synthetic methods for the preparation of such analogs. The have the active side chain moiety (5-R-hydroxyhexyl) of LSF and can have greater potency and oral bioavailability than LSF.

7 Claims, 21 Drawing Sheets

OTHER PUBLICATIONS

Abstract of Buu-Hoi at al., "Alkylation of phthalylhydrazine (2,3-dihydro-1,4-phthaiazinedione)," Receueil des Travaux Chimiques des Pays-Bas et de la Belgique 70:1099-1104 (1951).
Buu-Hoi et al., "Derives de phthaiazine d'interet biologique," Compt. Rend. 228:2037-2039 (1949).
Abstract of Buu-Hoi et al., "Phthaiazine derivatives of biological interest," Compt. Rend. 228:2037-2039 (1949).
Hall et al., "Targeting of human Tmolt4 leukemic type II IMP dehydrogenase by cyclic imide related derivatives," Archiv der Pharmazie 334(7):229-234 (2001).
Hall et al., "The antineoplastic activity of 2,3-dihydrophthalazine-1,4-dione and N-butyl-2,3-dihydrophthalazine-1,4-dione in human and murine tumor cells," Anti-Cancer Drugs 3(1):55-62 (1992).
Heine et al., "Novel Rearrangement of a Diaziridine," J. Org. Chem. 45(7):1317-1319 (1980).
Abstract of Heine et al., "Novel rearrangement of a diaziridine," J. Org. Chem. 45(7):1317-1319 (1980).
Heine et al., "Diaziridines III. Reactions of Some 1-Alkyl- and 1,1-Dialkyl-1H-diazirino[1,2-b]phthalazine-3,8-diones," J. Org. Chem. 39(22):3187-3191 (1974).
Horino et al., "ATP-sensitive potassium channel openers: synthesis and antihypertensive activity of 4-bicyclyloxybenzopyrans," Bioorg. & Med. Chem. Ltrs. 7(4):437-442 (1997).
Murthy et al., "The Hypolipidaemic Activity of a Series of 2,3-Dihydrophthaiazine-1,4-dione Derivatives in Rodents," Pharmaceutical Research 3(2):93-101 (1986).
Nada et al., "The behavior of tertiary phosphite esters towards 1,2-dihydro-3,6-pyridazinediones and 2,3-dihydro-1,4-phthalazinediones," Phosphorus, Sulfur and Silicon and the Related Elements 119:27-35 (1996).
Panea et al., "Biological active acylhydrazide I. The O-acyl derivatives nature of monoacylation products of cyclic maleic- and phthalic-hydrazide," Southern Brazilian J. Chem. 7(8):25-40 (1999).
Ratsimamanga et al., "Antituberculosis activity of derivatives of phthalylhydrazine," Archives Internationales be Pharmacodynamie et de Therapie 91:52-62 (1952).
International Search Report and Written Opinion for PCT/US2007/062968 dated Mar. 7, 2008.
International Preliminary Report on Patentability for PCT/US2007/062968 dated Sep. 1, 2009.
Nov. 23, 2011, Office Action in U.S. Appl. No. 12/550,124.
Apr. 26, 2011 Office Action in U.S. Appl. No. 12/550,124.
Hayashi et al., "On the N-Oxidation of 1-Alkoxy-phthalazines and 1,4-Dialkoxyphthalazines," J. Pharm. Soc. of Japan 82(4):584-590 (1962).
Ikeda et al., "Studies of Benzodiazines, XVI. Quaternary Salts of Substituted Phthalazines and Their Chemical Properties," Pharm. Soc. of Japan 88:521-526 (1968).

* cited by examiner

Scheme 3C

Scheme 3D

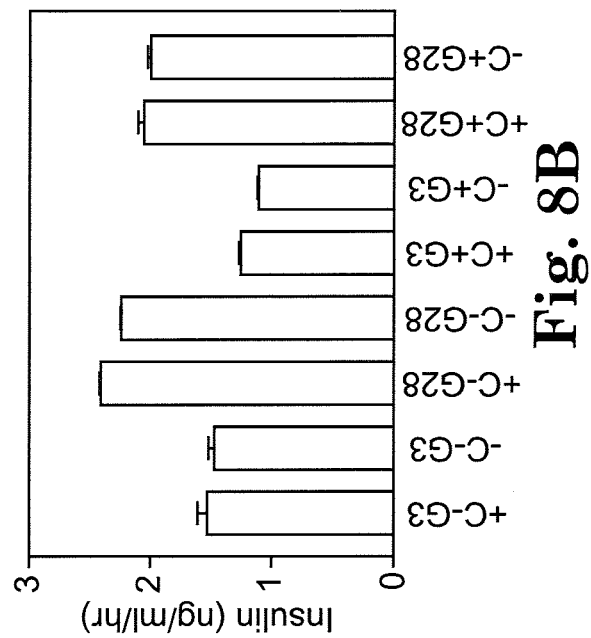
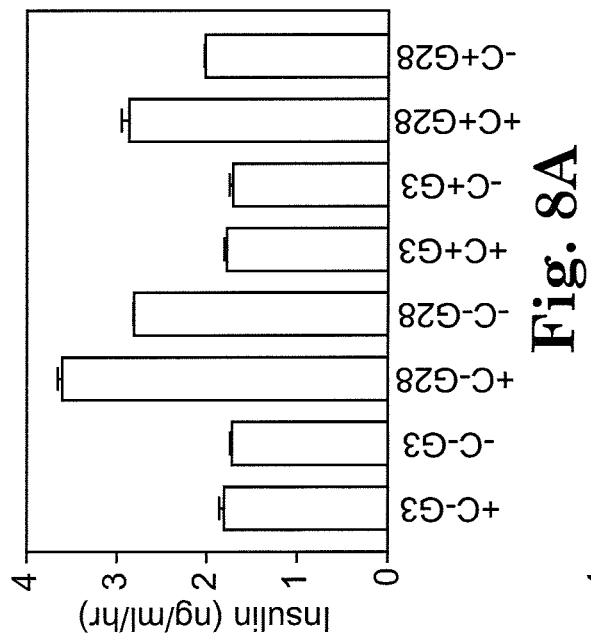
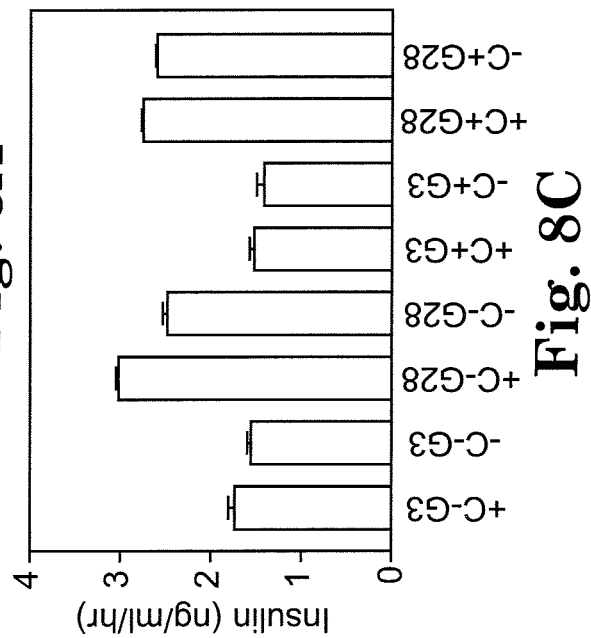

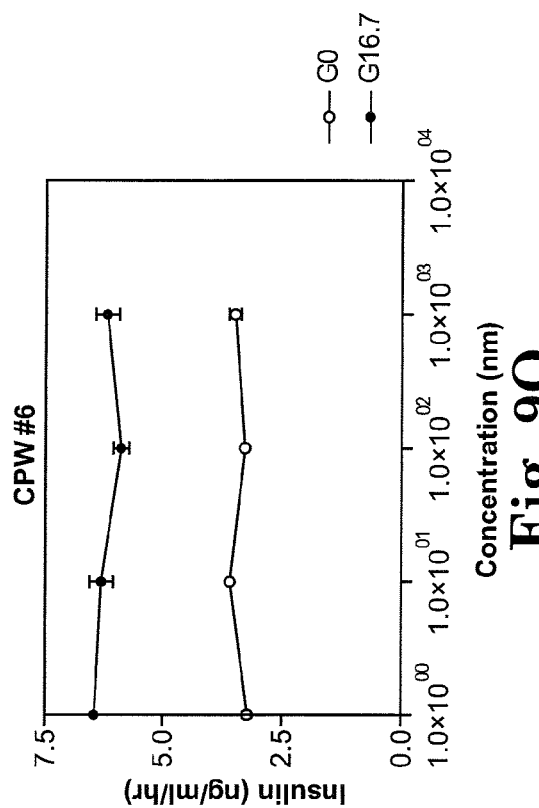
Fig. 9M
Fig. 9O
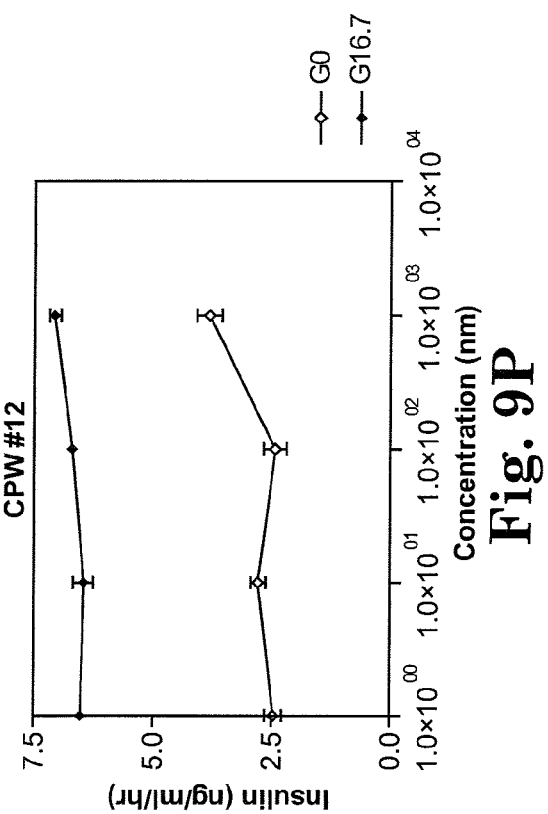
Fig. 9N
Fig. 9P
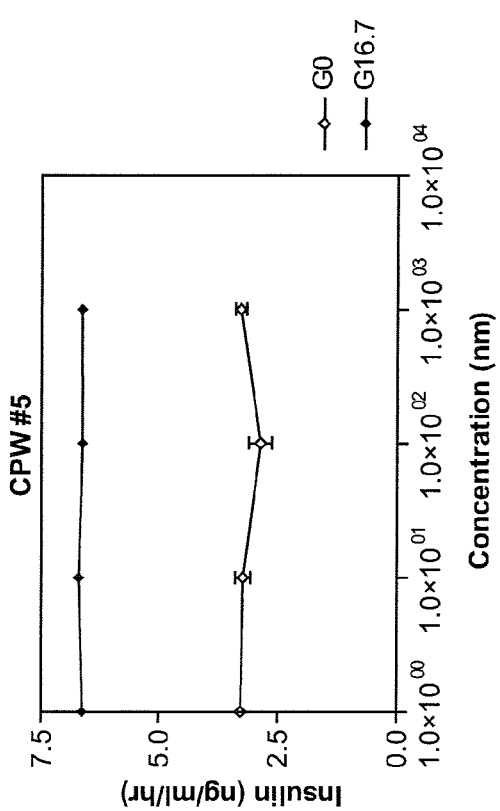
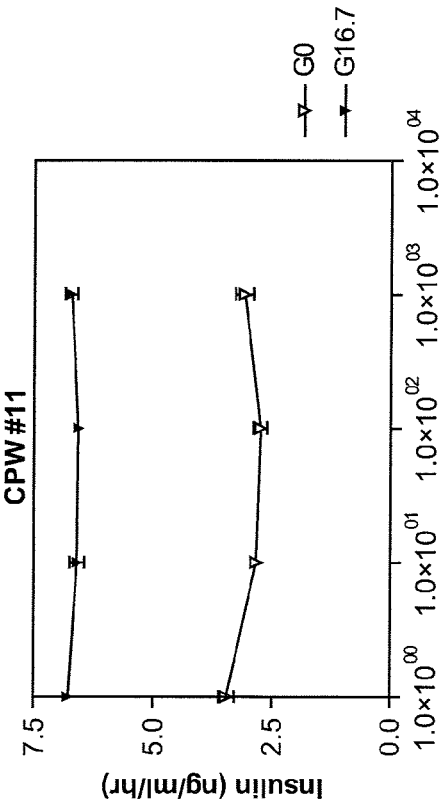

LISOFYLLINE ANALOGS AND METHODS FOR USE

RELATED APPLICATIONS

This application is a Continuation filed under 35 U.S.C. §111(a) of PCT/US2006/033777 filed on Aug. 29, 2006 and published in English as WO 2007/027719 A2 on Mar. 8, 2007; which International Application claims priority from provisional patent application Ser. No. 60/712,114, filed Aug. 29, 2005, these applications and publications are incorporated herein by reference.

GOVERNMENT FUNDING

The invention described herein was made with government support under Grant Numbers DK 63521 and R21DK 063521 awarded by the National Institute of Health. The United States Government has certain rights in the invention.

BACKGROUND OF THE INVENTION

Type 1 diabetes is an autoimmune disorder which results from the immune-mediated inflammatory destruction of insulin-producing β-cells in pancreatic islets. Although the specific pathogenic mechanisms in Type 1 diabetes are not known, it is believed that activated T cells and macrophages are required for the initiation. Once activated, macrophages secrete several inflammatory cytokines, such as interleukin 1β(IL-1β), interleukin 12 (IL-12) and tumor necrosis factor α (TNF-α), and trigger interferon-γ (IFN-γ) production from activated T cells (see Z. D. Yang, M. Chen, R. Wu, M. McDuffie, J. L. Nadler, *Diabetologia*, 2002, 45, 1307-1314). These cytokines are reported to be cytotoxic to β cells and enhance Th1-mediated inflammatory responses, which are believed to be responsible for the β cell destruction (see M. Chen, Z. D. Yang, R. Wu, J. L. Nadler, *Endocrinology*, 2002, 143(6), 2341-2348).

The anti-inflammatory compound Lisofylline (LSF; 1-(5-R-hydroxyhexyl)-3,7-dimethylxanthine)) has been shown to be able to protect β-cells from multiple inflammatory cytokine-mediated injuries by its ability to maintain insulin secretory capability and cell viability.

Agents such as Lisofylline may have clinical utility in preventing β-cell damage during the development of Type 1 diabetes. This hypothesis is supported by the studies that showed Lisofylline could significantly reduce spontaneous Type 1 diabetes development in the non-obese diabetic (NOD) mouse (see Yang). However, the disadvantages of Lisofylline may limit its clinical development because it is not orally bioavailable and has relatively weak potency. The structure of LSF is Formula I.

Currently, there is a need for novel, potent, and selective agents which There is a long felt need in the art for small molecules based on the Lisofylline backbone which have enhanced potency, selectivity, and oral bioavailability. The present invention satisfies this need.

SUMMARY

The present invention provides analogs of a Lysofylline (LSF), and synthetic methods for the preparation of such analogs. The analogs can have greater potency and oral bioavailability than LSF. The analogs have the active side chain moiety (5-R-hydroxyhexyl) of LSF. The invention also includes derivatives of LSF. LSF has formula I:

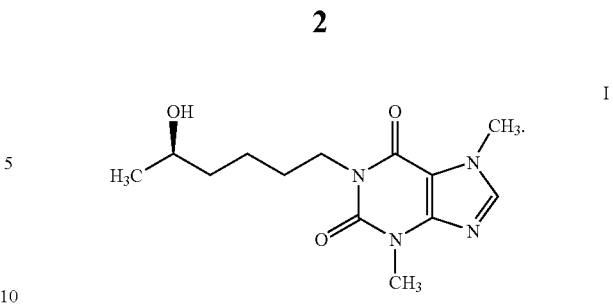

The disclosed analogs can be substituted with a variety of nitrogen-contained heterocyclic compounds or on the hydroxyl group of the side chain. Accordingly, the invention provides 1-substituted 5-hexanol compounds having additional substitution on the hydroxyl group. The compounds have the formula II:

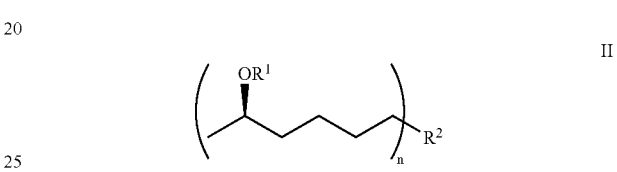

where $R^1$ is hydrogen or a group having the formula —C(=O)$R^3$, wherein $R^3$ is lower alkyl. $R^2$ is selected from the group consisting of

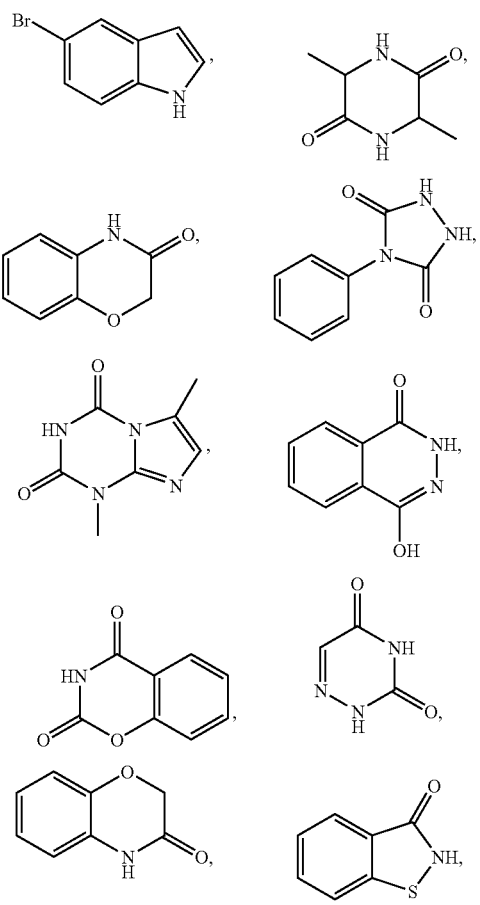

-continued

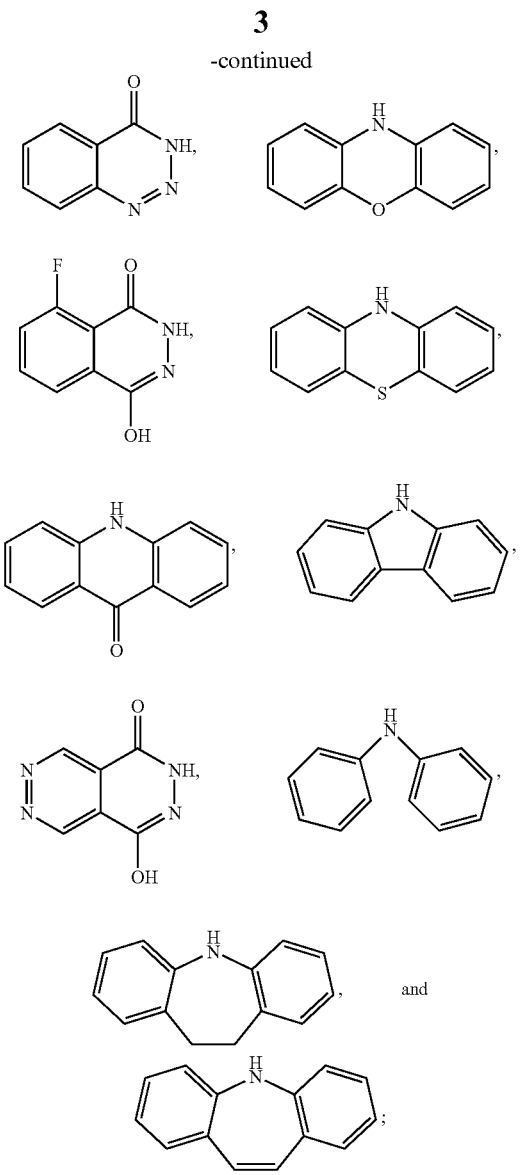

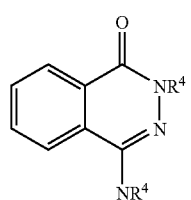

and n is 1 or 2, or a pharmaceutically acceptable salt thereof.

In another embodiment, the present invention provides analogs having formula

III

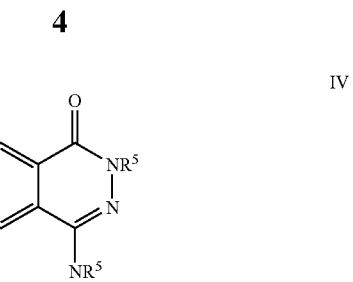

where each $R^4$ is independently hydrogen or —$(CH_2)_m$—$OR^1$, where $R^1$ is hydrogen or a group having the formula —$C(=O)R^3$, wherein $R^3$ is lower alkyl and m is an integer from 2 to about 22, provided that at least one $R^4$ group is not hydrogen.

In another embodiment, the present invention provides analogs having formula IV:

IV where each $R^5$ is independently hydrogen or —$(CH_2)_i$—$(CHOR^1,)$—$(CH_2)_j$—$CH_3$, where $R^1$ is hydrogen or a group having the formula —$C(=O)R^3$, wherein $R^3$ is lower alkyl, i is an integer from 1 to about 20, and j is an integer from 0 to about 20, provided that the sum of i and j in each $R^5$ group is from 2 to about 22 and at least one $R^5$ group is not hydrogen.

In another embodiment, the present invention provides analogs of LSF having the ability to protect cell viability, particularly the ability to protect pancreatic β-cells. Thus, the disclosed analogs can allow the pancreas to maintain its insulin secretory capability.

In another embodiment, the present invention provides analogs of LSF which are effective in treating Type 1 diabetes. In another embodiment, the present invention provides analogs of LSF which can inhibit the development of Type 1 diabetes.

In another embodiment, the present invention provides analogs of LSF which are effective in treating Type 1 diabetes. In another embodiment, the present invention provides analogs of LSF which can lead to reversal of type I diabetes by allowing the body to regenerate beta cells.

In another aspect, the present invention also provides:
a pharmaceutical composition comprising a compound of formula II, formula III, formula IV, or pharmaceutically acceptable salts thereof, and a pharmaceutically acceptable carrier or excipient (the composition preferably comprises an effective amount of the compound or salt);

a method of treating or preventing Type 1 diabetes, comprising administering to a mammal (e.g., a human) in need of such treatment, a compound of formula II, formula III, formula IV, or pharmaceutically acceptable salts thereof;

a method for protecting cell viability, particularly the ability to protect pancreatic β-cells comprising contacting (in vitro or in vivo) the cells with an effective protective amount of a compound of formula II, formula III, formula IV, or a pharmaceutically acceptable salt thereof;

a compound of formula II, formula III, formula IV, or a pharmaceutically acceptable salt thereof for use in medical treatment (e.g., the treatment of Type 1 diabetes); and the use of a compound of formula II, formula III, formula IV, or a pharmaceutically acceptable salt thereof to prepare a medicament for treating Type 1 diabetes in a mammal (e.g., a human).

The disclosed analogs can be useful in the treatment of inflammatory and autoimmune diseases. Non-limiting examples of such diseases include atherosclerosis, type 2 diabetes, disorders associated with visceral obesity such as non-alcoholic steatohepatitis (NASH), multiple sclerosis, inflammatory bowel disease, psoriasis, rheumatoid arthritis, Alzheimer's disease and the like.

The invention also provides methods for testing the activity of the disclosed compounds. Methods not disclosed are known to those of ordinary skill in the art. One of ordinary skill will appreciate that many techniques are available to determine whether the compounds produce the desired result.

The invention also provides a kit for administering the disclosed compounds.

The invention also provides novel intermediates and processes disclosed herein that are useful for preparing analogs of formula II, formula III, or formula IV, including the generic and specific intermediates as well as the synthetic processes described in the Charts and Examples herein.

BRIEF DESCRIPTION OF THE DRAWINGS

FIG. 7A illustrates the basal-stimulated Insulin Release. FIG. 7B illustrates the glucose-stimulated Insulin Release. FIG. 7C illustrates the ATP concentrations and FIG. 7D illustrates the β-cell viability.

FIGS. 8a-8c illustrate the ability of the disclosed analogs to stimulate insulin release from β-cells.

DETAILED DESCRIPTION

Figure 1A:
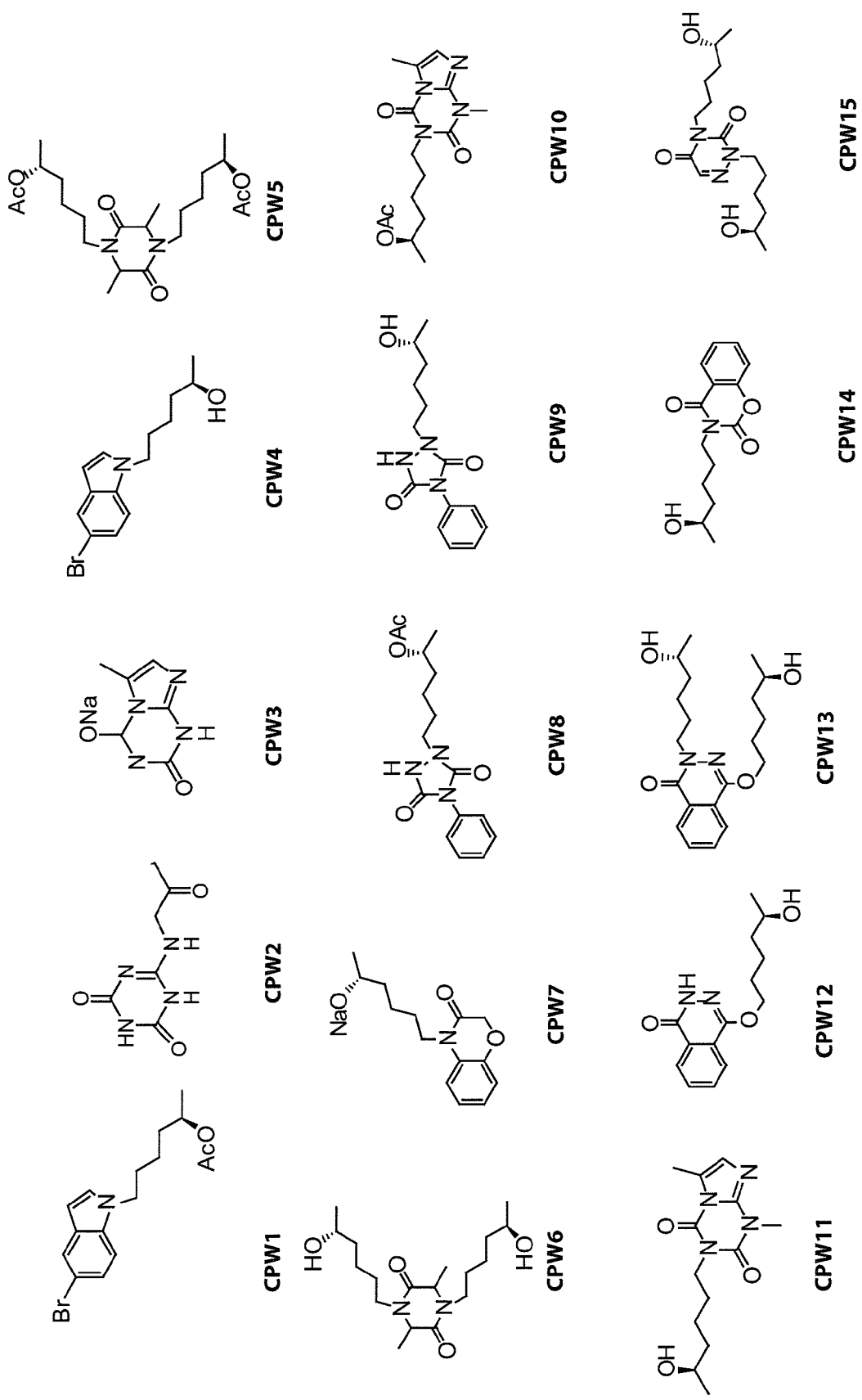
FIGS. 1A-1B depicts exemplary of compounds of the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein.

In describing and claiming the invention, the following terminology will be used in accordance with the definitions set forth below.

For purposes of the description of this invention, the articles "a" and "an" are used herein to refer to one or to more than one (i.e., to at least one) of the grammatical object of the article. By way of example, "an element" means one element or more than one element.

A disease or disorder is "alleviated" if the severity of a symptom of the disease, condition, or disorder, or the frequency with which such a symptom is experienced by a subject, or both, are reduced.

As used herein, an "analog" of a chemical compound is a compound that, by way of example, resembles another in structure but is not necessarily an isomer (e.g., 5-fluorouracil is an analog of thymine).

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder.

A tissue "normally comprises" a cell if one or more of the cell are present in the tissue in an animal not afflicted with a disease or disorder.

The terms "compound" or "analog," are used interchangeably. As used herein, these terms refer to any type of substance or agent that is commonly considered a drug, or a candidate for use as a drug, combinations, and mixtures of the above, as well as polypeptides and antibodies of the invention.

As used herein, a "derivative" of a compound refers to a chemical compound that may be produced from another compound of similar structure in one or more steps, as in replacement of a hydrogen atom by an alkyl, acyl, or amino group.

As used herein, an "effective amount" means an amount sufficient to produce a selected effect.

The use of the word "detect" and its grammatical variants is intended to refer to measurement of the species without quantification, whereas use of the word "determine" or "measure" with their grammatical variants are meant to refer to measurement of the species with quantification. The terms "detect" and "identify" are used interchangeably herein.

As used herein a "disease" is a state of health of an animal wherein the animal cannot maintain homeostasis, and wherein if the disease is not ameliorated then the animal's health continues to deteriorate.

In contrast, as used herein a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, a "functional" analog or molecule is a molecule in a form in which it exhibits a property or activity by which it is characterized.

As used herein, the term "inhibit," refers to the ability of the disclosed compounds to reduce or impede a described function. Preferably, inhibition is by at least 10%, more preferably by at least 25%, even more preferably by at least 50%, and most preferably, the function is inhibited by at least 75%.

As used herein, "instructional material(s)" includes a publication, a recording, a diagram, or any other medium of expression which can be used to communicate the usefulness of the disclosed analogs in the kit for effecting alleviation of the various diseases or disorders recited herein. Optionally, or alternately, the instructional material may describe one or more methods of alleviating the diseases or disorders in a cell or a tissue of a mammal. The instructional material of the kit may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, the term "purified" and similar terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans. Examples of these and other pharmaceutically acceptable carriers are described in Remington's Pharmaceutical Sciences (1991, Mack Publication Co., New Jersey).

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

As used herein, the terms "treating or treatment" includes prophylaxis of the specific disorder or condition, or alleviation of the symptoms associated with a specific disorder or condition and/or preventing or eliminating said symptoms.

As used herein, a "prophylactic" treatment is a treatment administered to a subject who does not exhibit signs of a disease or exhibits only early signs of the disease for the purpose of decreasing the risk of developing pathology associated with the disease.

As used herein, a "therapeutic" treatment is a treatment administered to a subject who exhibits signs of pathology for the purpose of diminishing or eliminating those signs.

As used herein, a "therapeutically effective amount" of a compound or analog is an amount of compound which is sufficient to provide a beneficial effect to the subject to which the compound is administered.

As used herein, the term "halogen" or "halo" includes bromo, chloro, fluoro, and iodo. The term "haloalkyl" as used herein refers to an alkyl radical bearing at least one halogen substituent, for example, chloromethyl, fluoroethyl or trifluoromethyl and the like.

The term "lower alkyl" refers to alkyl groups having from one (1) to (6) carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

It will be appreciated by those skilled in the art that the disclosed compounds having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine cADPR agonist or antagonist activity using the standard tests described herein, or using other similar tests which are well known in the art.

The compounds of the present invention may exist in tautomeric forms and the invention includes both mixtures and separate individual tautomers. For example the following structure:

is understood to represent a mixture of the structures:

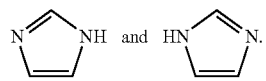

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In another embodiment, the present invention provides kits for use in administering or using the disclosed compounds.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Exemplary values listed below for radicals, substituents, and ranges, are for illustration only; they do not exclude other defined values or other values within defined ranges for the radicals and substituents.

For example, $(C_1-C_6)$alkyl can be methyl, ethyl, propyl, isopropyl, butyl, iso-butyl, sec-butyl, pentyl, 3-pentyl, hexyl and the like.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours, "rt" for room temperature, and "rac" for racemic mixture).

The invention also provides compounds of formula II, formula III, or formula IV, for use in medical therapy.

A value for $R^1$ is hydrogen or $—C(=O)R^3$, wherein methyl, ethyl or propyl.

Another value for $R^3$ is methyl, or ethyl.

Another value for $R^3$ is methyl.

Another value for $R^1$ is hydrogen.

A value for $R^2$ is

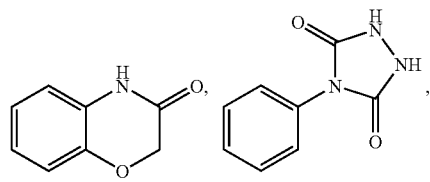

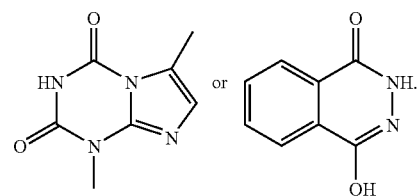

In one aspect, the disclosed analogs have the formulas:

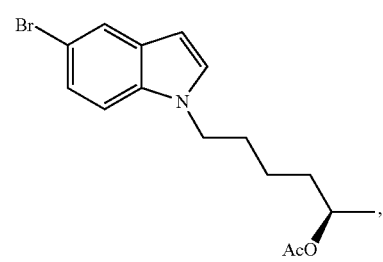

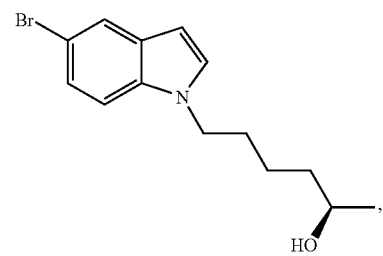

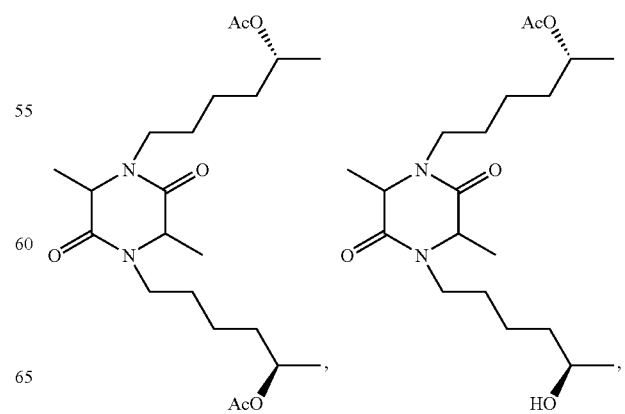

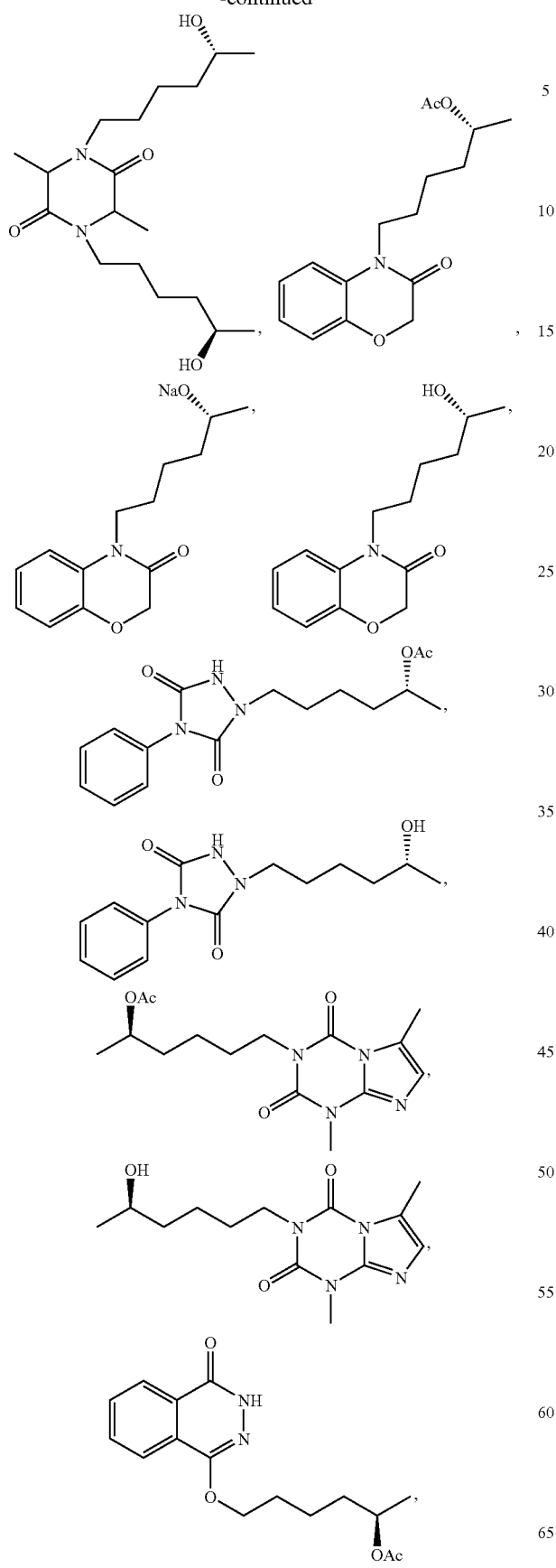
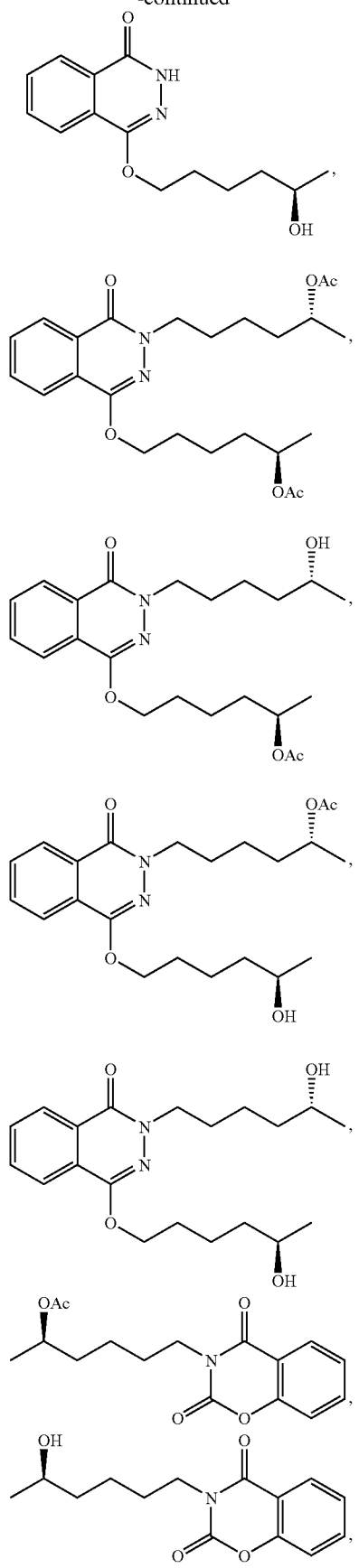

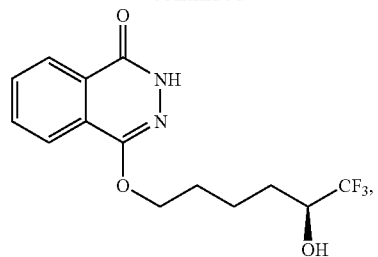
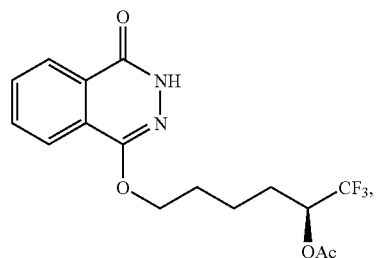
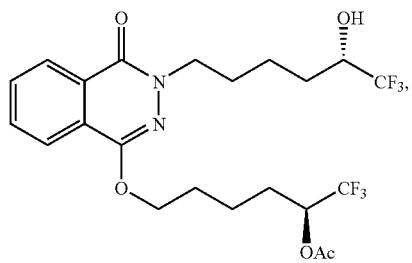
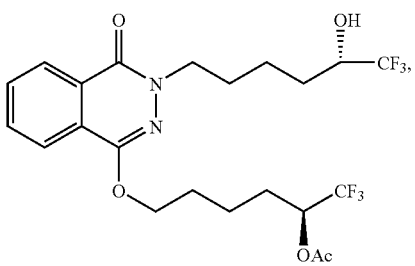
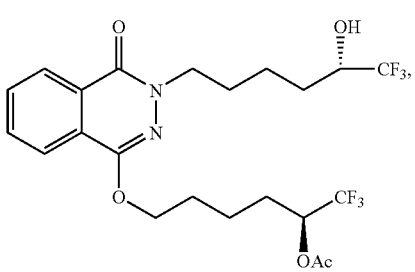
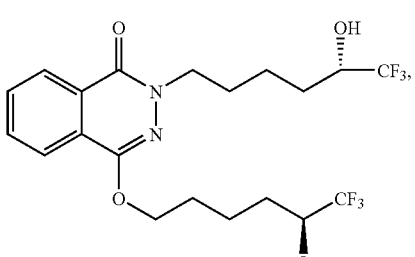
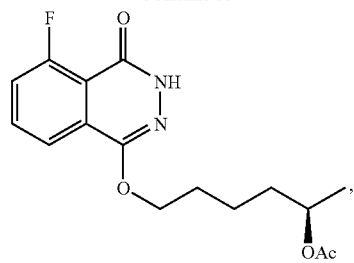
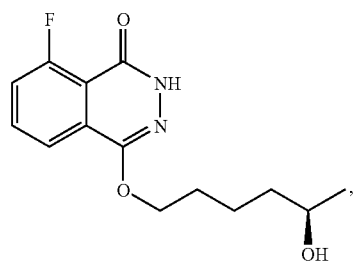
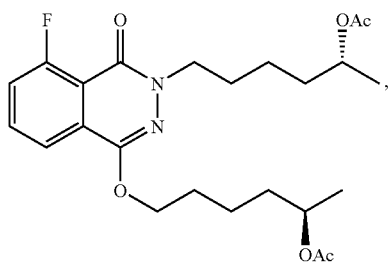
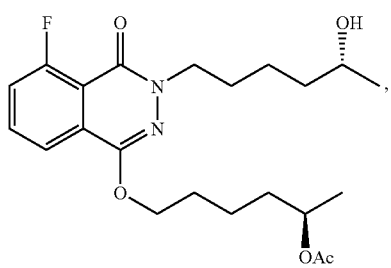
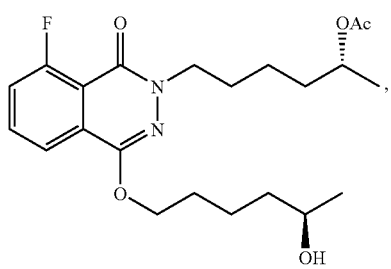
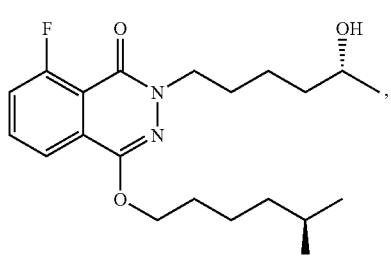

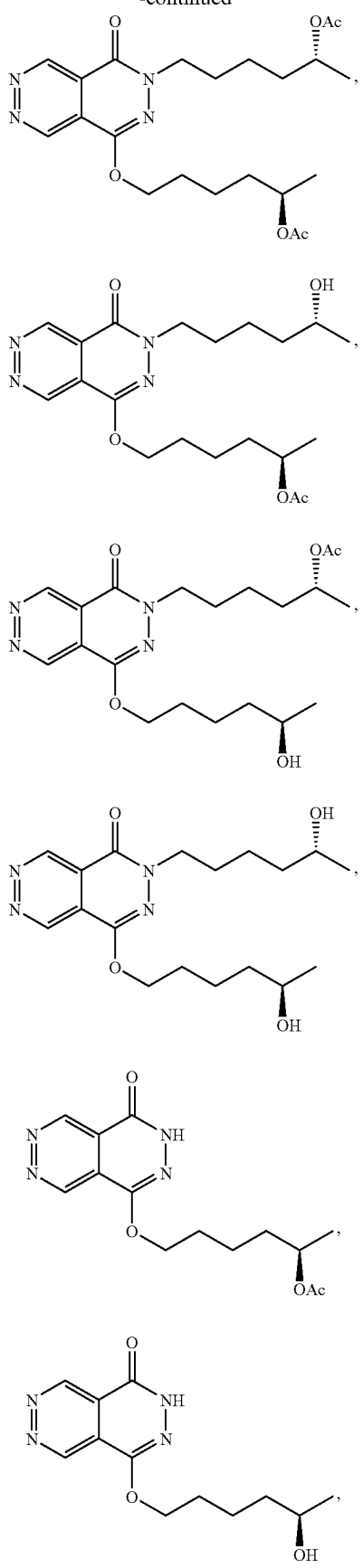

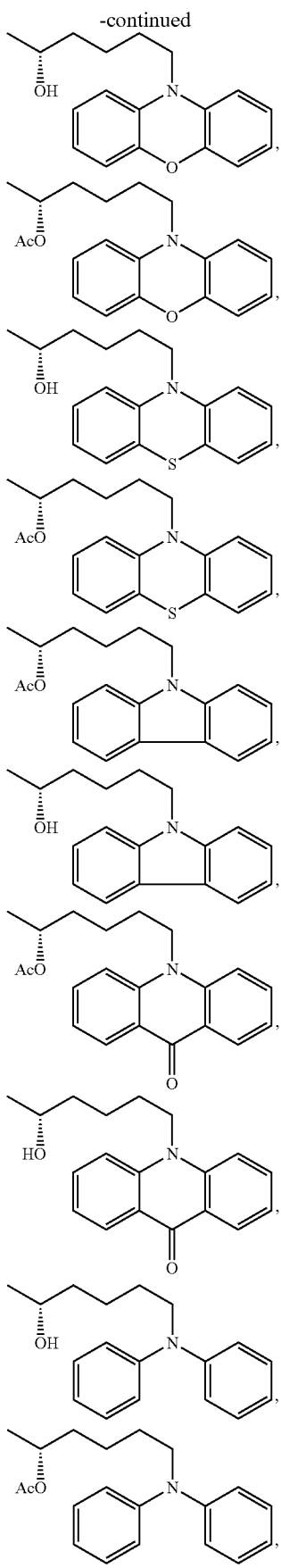
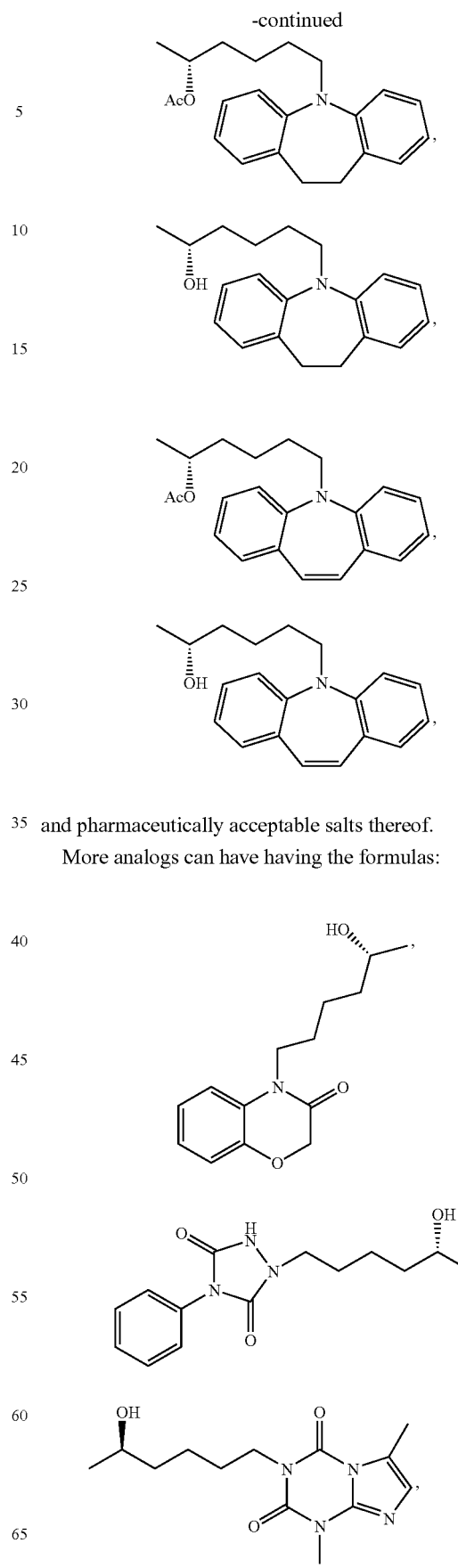
and pharmaceutically acceptable salts thereof.
More analogs can have having the formulas:

-continued

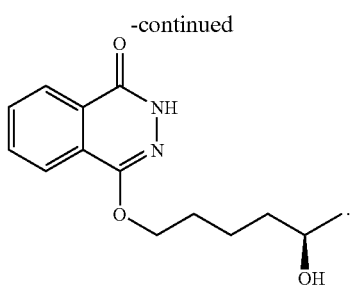

Processes for preparing analogs of formula II, formula III, or formula IV, are provided as further embodiments and are illustrated by the following procedures in which the meanings of the generic radicals are as given above unless otherwise qualified. A general scheme for preparing the disclosed analogs having formula II is provided in Scheme 1:

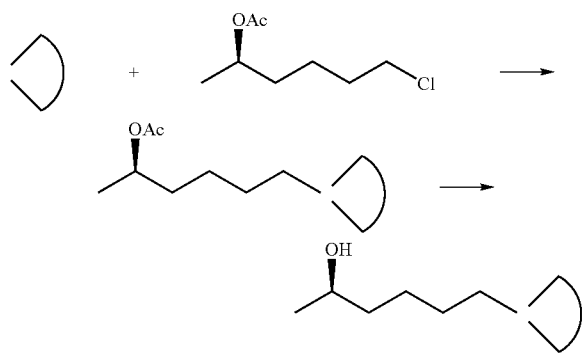

Figure 2:
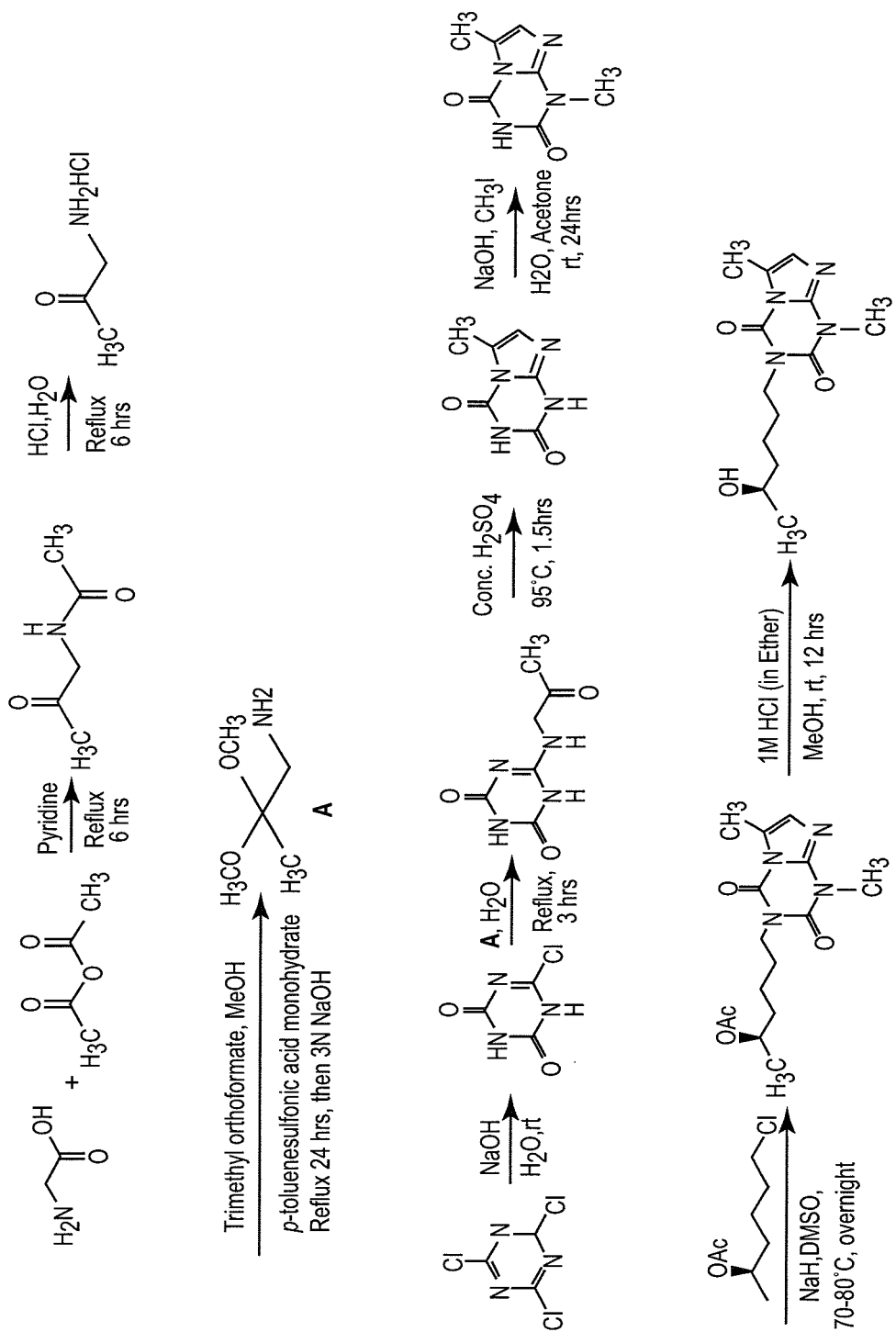
FIG. 2 illustrates a scheme for preparing compound CPW11.
Figure 3A:
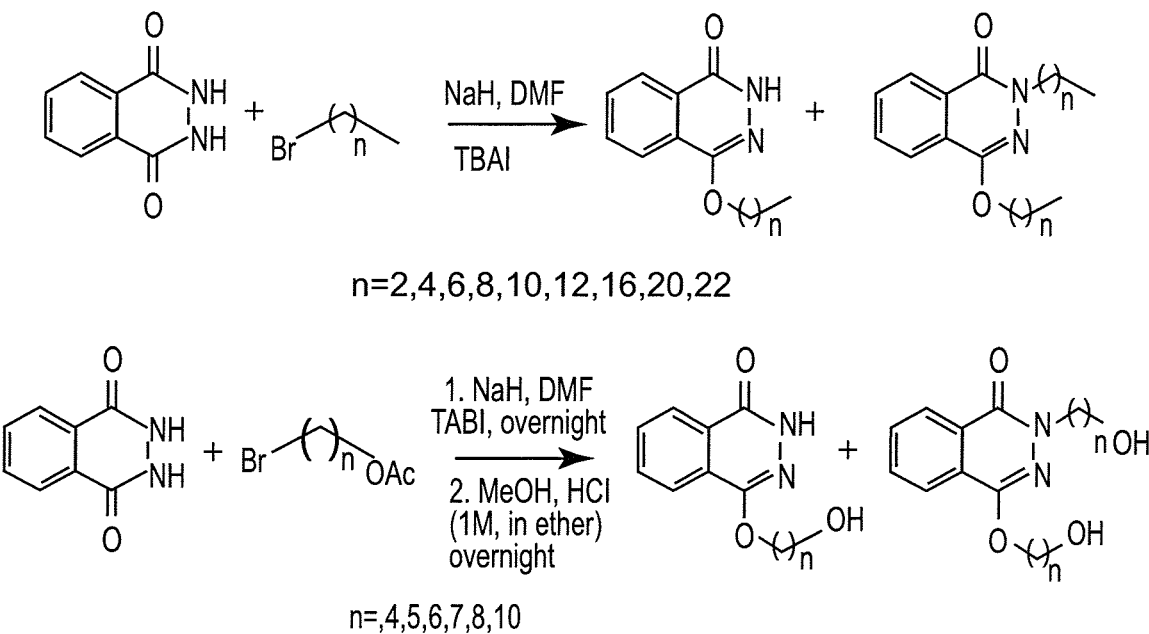
FIGS. 3A-3D illustrate schemes for preparing analogs having an $R^2$ group based on 2,3-dihydro-phthalazine-1,4-dione.
Figure 3B:
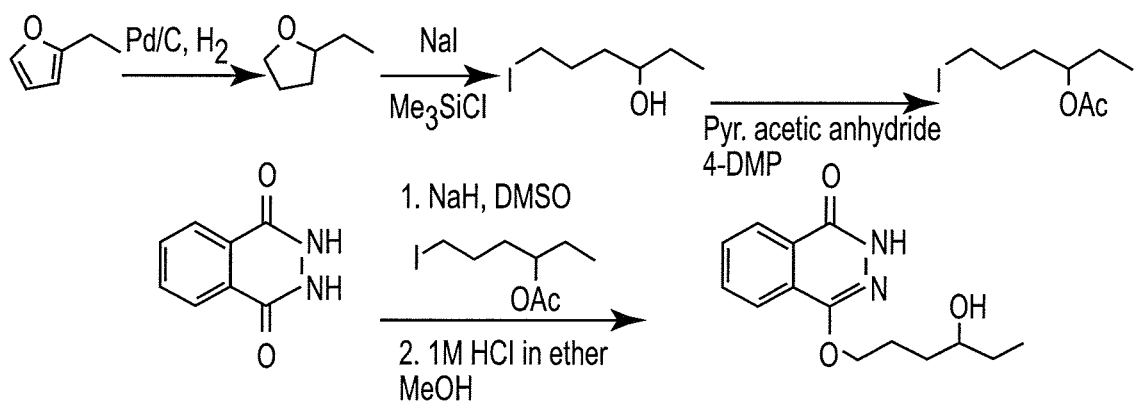
Figure 3C:
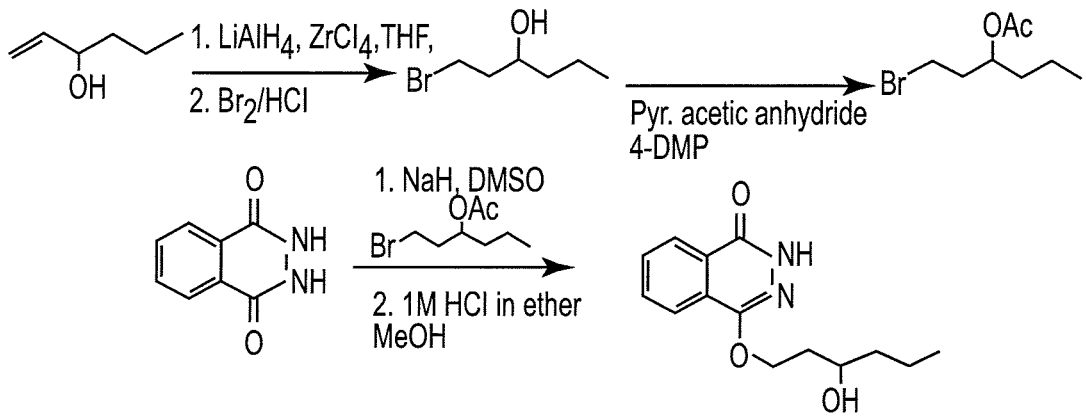
Figure 3D:
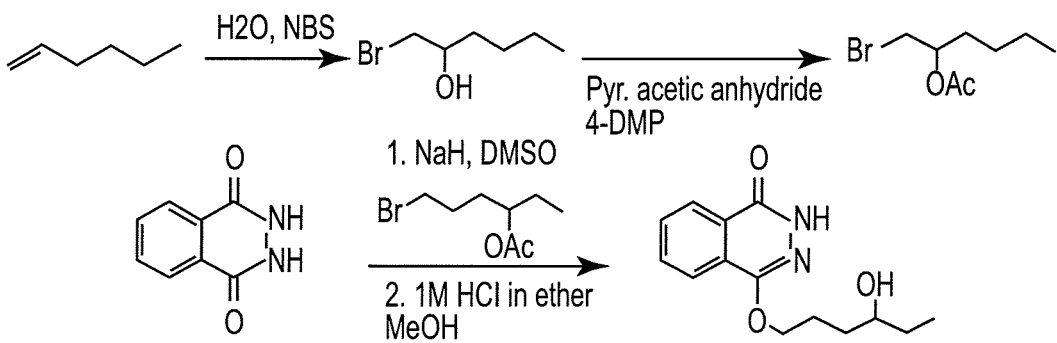

Scheme 2 (FIG. 2) provides a synthetic scheme route to prepare analog 11. The preparation of additional analogs having formula III, or formula IV, are illustrated in FIGS. 3A-3D and FIG. 4.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions (suspensions) or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. This dispersion or solution may be formulated according to the known art, and may comprise, in addition to the active ingredient, additional ingredients such as the dispersing agents, wetting agents, or suspending agents. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. Other acceptable diluents and solvents include, but are not limited to, Ringer's solution, isotonic sodium chloride solution, and fixed oils such as synthetic mono- or di-glycerides. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile solutions are prepared by incorporating the active compound in the required amount in the appropriate solvent with various of the other ingredients enumerated above, as required, followed by filter sterilization. In the case of sterile powders for the preparation of sterile solutions, the preferred methods of preparation are vacuum drying and the freeze drying techniques, which yield a powder of the active ingredient plus any additional desired ingredient present in the previously sterile-filtered solutions. The sterile solutions or powders can be combined with suitable carriers and administered via injection. In addition, the sterile solutions or powders can be combined with suitable carriers and/or propellants and administered via inhalation.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a solution or suspension, will be from about 0.1-25 wt %, preferably from about 0.5-10 wt %. The concentration in a semi-solid or solid composition such as a gel or a powder will be about 0.1-5 wt %, preferably about 0.5-2.5 wt %.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 20 mg/kg, e.g., from about 1 to about 18 mg/kg of body weight per day, such as 3 to about 16 mg per kilogram body weight of the recipient per day, preferably in the range of 6 to 14 mg/kg/day, most preferably in the range of 9 to 11 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by administration of a plurality of tablets.

Compounds which are identified using any of the methods described herein may be formulated and administered to a subject for treatment of any of the diseases and disorders described herein. However, the use of the disclosed compounds should not be construed to include only the diseases and disorder described herein. Preferably, the subject is a human.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions is contemplated include, but are not limited to, humans and other primates, and mammals, including commercially relevant mammals such as cattle, pigs, horses, sheep, cats, and dogs.

A pharmaceutical composition may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition may further comprise one or more additional pharmaceutically active agents. Particularly contemplated additional agents include anti-emetics and scavengers such as cyanide and cyanate scavengers.

Controlled- or sustained-release formulations of the pharmaceutical compositions herein may be made using conventional technology.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein can be readily selected for use with the pharmaceutical compositions. Thus, single unit dosage forms suitable for oral administration, such as tablets, capsules, gelcaps, and caplets that are adapted for controlled-release are encompassed by the present invention.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds.

Powdered and granular formulations of a pharmaceutical preparation may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A formulation of a pharmaceutical composition suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, a paste, a gel, a toothpaste, a mouthwash, a coating, an oral rinse, or an emulsion. The terms oral rinse and mouthwash are used interchangeably herein.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition which are suitable for oral administration may be prepared, packaged, and sold either in liquid form or in the form of a dry product intended for reconstitution with water or another suitable vehicle prior to use.

Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

A pharmaceutical composition may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. See Genaro, ed., 1985, Remington's Pharmaceutical Sciences, Mack Publishing Co., Easton, Pa., which is incorporated herein by reference.

The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type, and age of the subject, etc.

The invention also provides a pharmaceutical pack or kit comprising one or more containers filled with one or more of the ingredients of the disclosed pharmaceutical compositions. In accordance with one embodiment, a kit is provided for treating a subject in need of immuno-modulation. Preferably, the subject is a human. In one embodiment, the kit comprises one or more of the SIP analogs of the present invention and may also include one or more known immunosuppressants. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

Although any methods and materials similar or equivalent to those described herein can be used in the practice or testing of the present invention, the preferred methods and materials are described herein.

In accordance with the present invention, as described above or as discussed in the Examples below, there can be employed conventional clinical, chemical, cellular, histochemical, biochemical, molecular biology, microbiology, and recombinant DNA techniques which are known to those of ordinary skill in the art. Such techniques are fully explained in the literature.

EXAMPLES

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out some embodiments of the present invention, and are not to be construed as limiting in any way the remainder of the disclosure. Therefore, the examples should be construed to encompass any and all variations which become evident as a result of the teaching provided herein.

Example 1

LSF Analogs

Figure 1B:
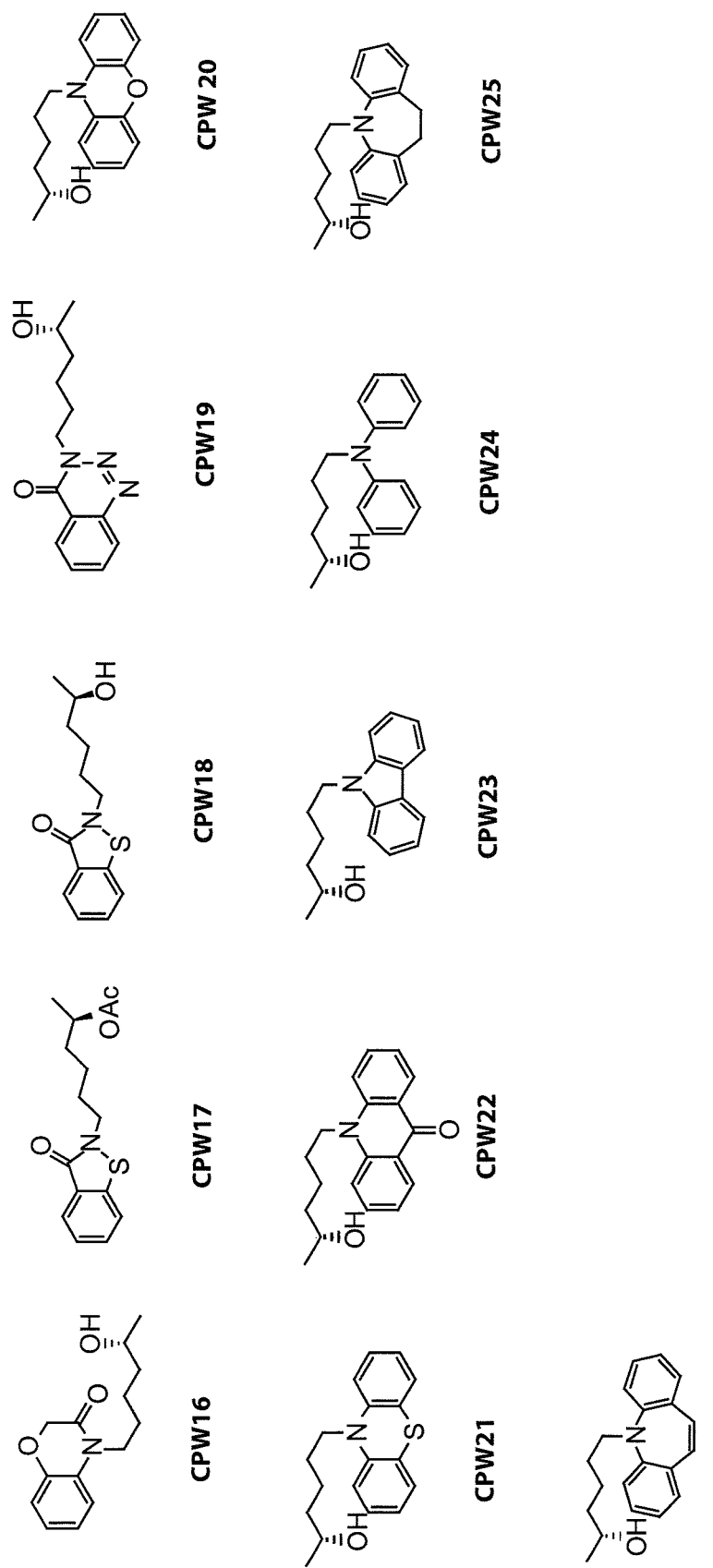

The side chain moiety (5-R-hydroxyhexyl) was kept constant and a variety of nitrogen-contained heterocyclic compounds, including xanthine-like (5-aza-7-deazaxanthine-LSF) and non-xanthine-like skeletons, were prepared for substitution with the hydroxyhexyl group. Most of the heterocyclic compounds were commercially available. 5-aza-7-deazaxanthine (in compounds 10 and 11), which was synthesized from a 1,3,5-triazine derivative, cyanuric chloride. See J. D. Hepworth. *Org. Synth.* 5, 27-29; R. Calabretta, C. Giordano, C. Gallina, V. Morea, V. Consalvi and R. Scandurra. *Eur. J. Med. Chem.* 1995, 30, 931-941; S. Horrobin. *J. Chem. Soc.* 1963, 4130-4145; and S. H. Kim, D. G. Bartholomew, and L. B. Allen. *J. Med. Chem.* 1978, 21(9), 883-888. The general scheme for synthesis of the LSF analogs is provided in scheme 1. Exemplary compounds are depicted in FIG. 1. The synthesis of compound 11 (CPW11) is illustrated in Scheme 2, FIG. 2.

Example 2

Biological Evaluations of LSF Analogs

Figure 6:
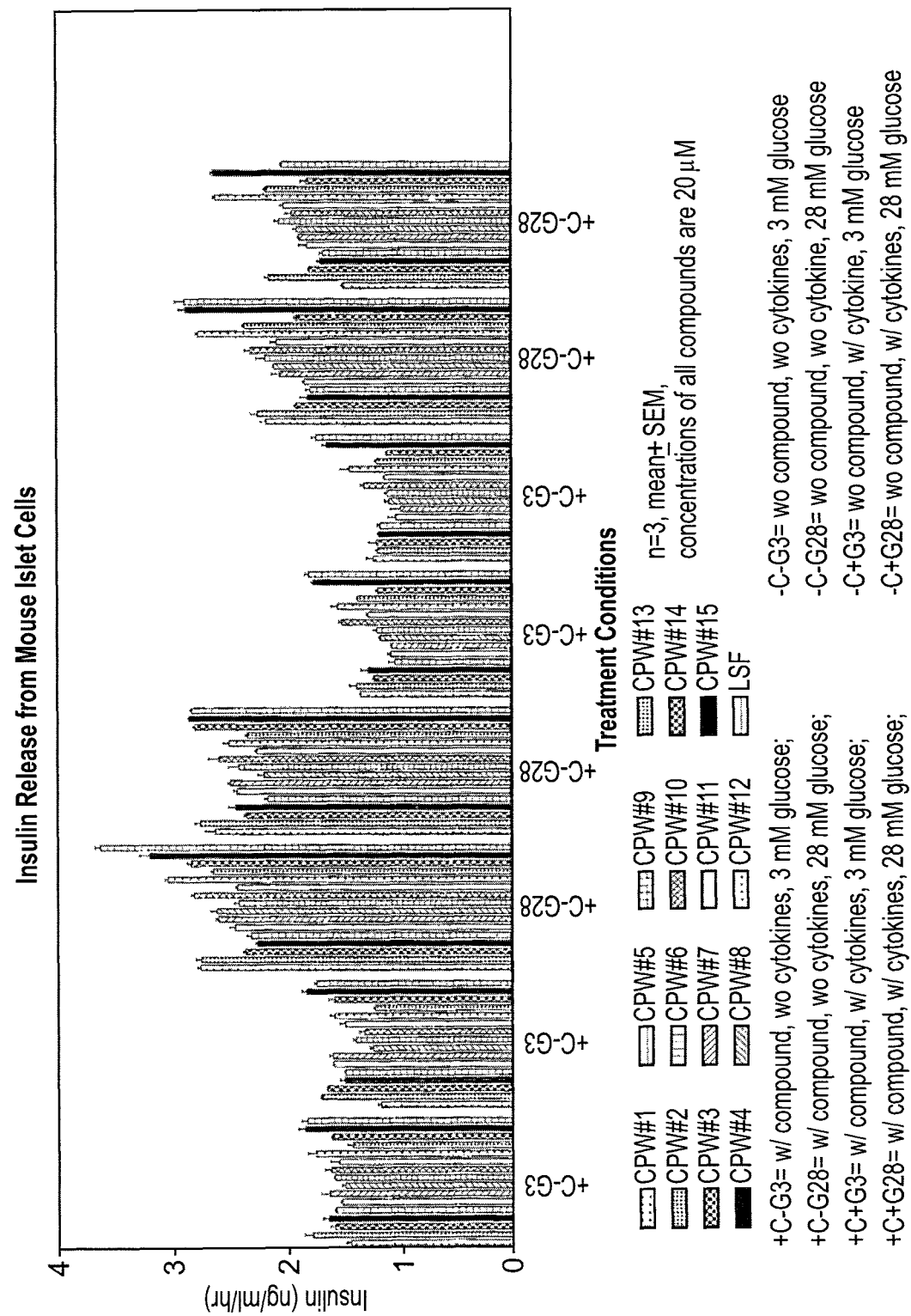
FIG. 6 illustrates the release of insulin from mouse islet cells.
Figure 7A:
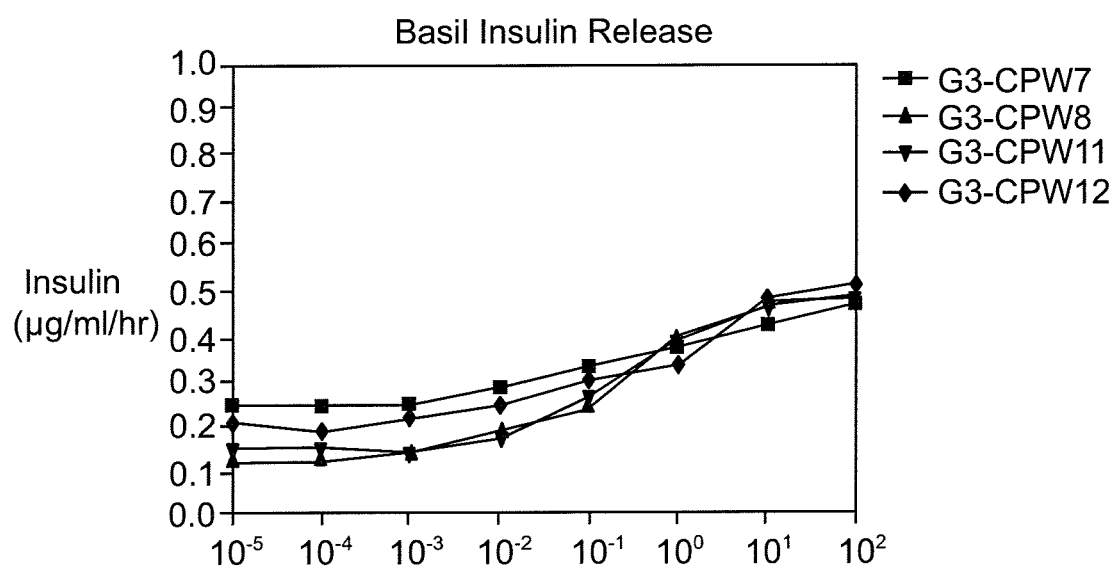
FIGS. 7A-7D illustrate the release of insulin from mouse islet cells.
Figure 7B:
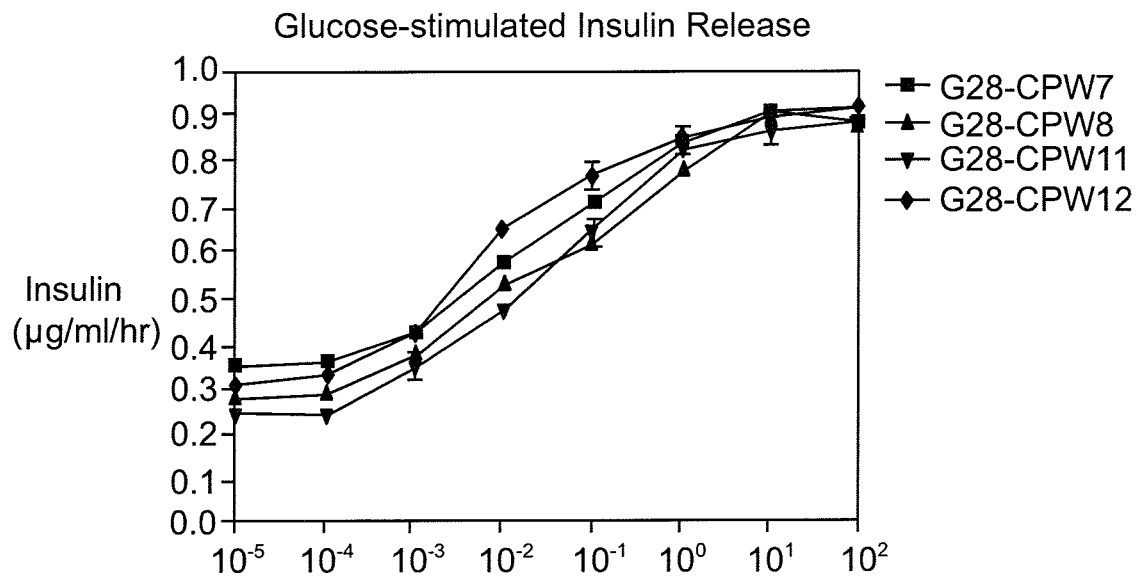
Figure 7C:
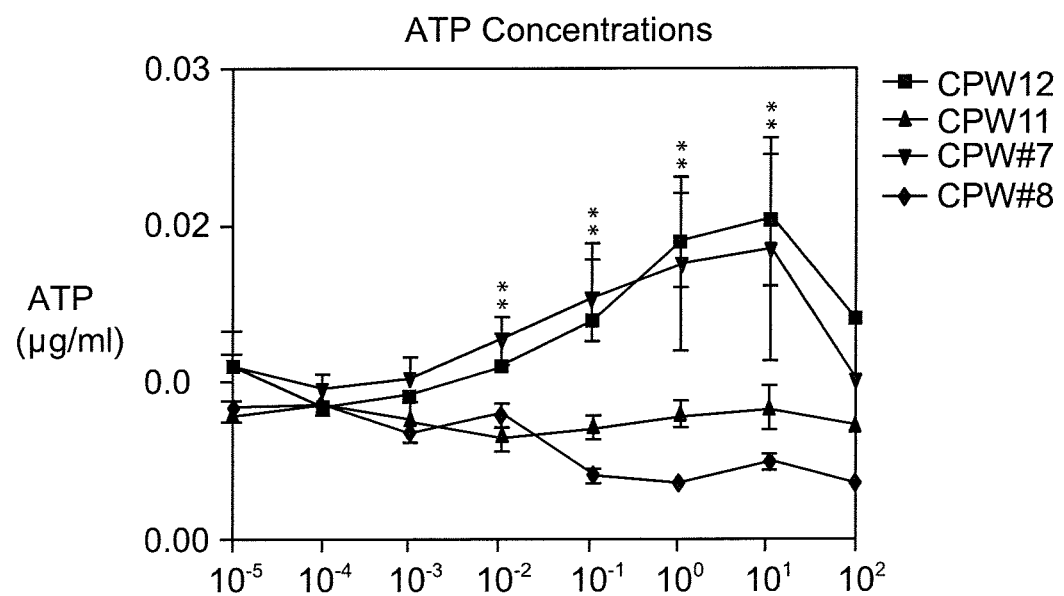
Figure 7D:
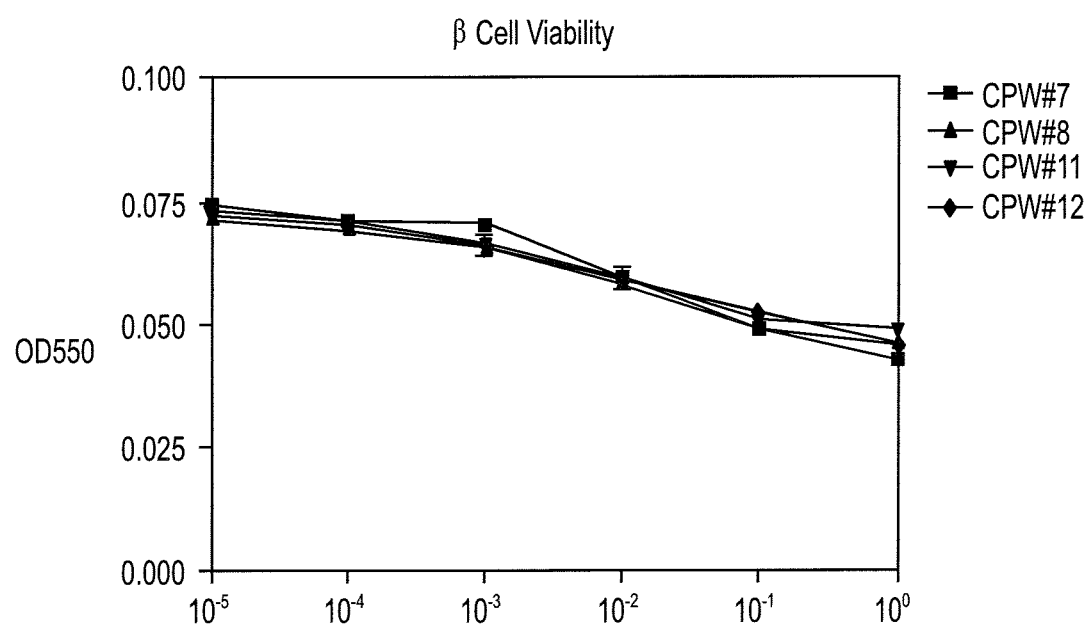

The disclosed analogs (CPW1-15) were evaluated in pancreatic β cell lines for apoptosis protection after treatment with inflammatory cytokines (reflected by reduced OD450) and insulin release (see FIGS. 5 and 6). For the protective effect of β-cells, some analogs showed comparative potency with LSF and additional analogs were able to protect cells at low concentrations (nm and lower; see FIG. 5). For the insulin release assay, some compounds demonstrated effects similar to those of LSF in response to glucose (CPW1-15; FIG. 6).

Further evaluations were performed for some of the LSF analogs in MDS assays, solubility, oral bioavailability, and stability (see Table 1).

TABLE 1 rCYP450 Inhibition and Metabolic Stabilities

| Compound No. | Formula Weight | rCYP % Inhibition | | | | | Metabolic Stability |
| | | 1A2 | 2C9 | 2C19 | 2D6 | 3A4 | Percent Remaining |
| --- | --- | --- | --- | --- | --- | --- | --- |
| CPW1 | 338.24 | 58% | 86% | 99% | 80% | 57% | 0% |
| CPW4 | 296.2 | 56% | 38% | 94% | 50% | 32% | 0% |
| CPW6 | 342.47 | 13% | 3% | 14% | 16% | 14% | 77% |
| CPW7 | 271.29 | 12% | 5% | 12% | 8% | 12% | na |
| CPW8 | 319.36 | 7% | 5% | 24% | 10% | 12% | 45% |
| CPW9 | 277.32 | 5% | −12% | 1% | 2% | −4% | 106% |
| CPW11 | 280.32 | 13% | 12% | 21% | 3% | 0% | 82% |
| CPW12 | 262.3 | 18% | 30% | 30% | 12% | 4% | 75% |
| CPW20 | 283.36 | 95% | 86% | 98% | 73% | 50% | 19% |
| CPW13 | 362.46 | 25% | 92% | 89% | −28% | −159% | 38% |

Analogs having greater than 50% inhibitory activity were considered to have high activity; analogs having from 20-49% inhibitory activity were considered to have medium activity; and analogs having less than 20 inhibitory activity were considered to have low activity Example 3

Biological Evaluations of LSF Analogs in Human Islets

Four compounds (CPW7, CPW8, CPW11, and CPW12) were also evaluated on human islets for the induction of insulin secretion, intracellular ATP concentrations and the effect of reducing cell death exposed to cytokines (combination of human IL-1β, IFN-γ, and TNF-α). The results are illustrated in FIGS. 7A-7D.

The results of the testing indicate that CPW12 indicates that there were positive effects in β-cell protection and insulin release on mouse islet cell line, the analog shows low cytochrome p450 inhibition (it was a safe compound with low potential for drug interactions). The Caco-2 permeability test results shows CPW12 could be orally absorbed from the GI track, which is consistent with good oral bioavailability. The CPW12 analog shows acceptable stability and solubility.

In the evaluation on human islet, CPW12 shows positive effects to improve insulin secretion in the presence of inflammatory cytokines and has a beneficial effect in maintaining mitochondrial function and cell viability in human β-cells.

Example 4

Effects of LSF and Analogs on D-Cells

The effects of LSF analogs on β-cells in the mouse insulin-secreting INS-1 cell line were investigated. Cells were maintained in RPMI 1640 medium (Life Technologies, Inc., Gaithersburg, Md.) supplemented with 10% heat-inactivated FBS, 10 mm HEPES, 200 μm L-glutamine, 1 mm sodium pyruvate, 5 nm 2-mercaptoethanol, 50 U/ml penicillin, and 50 μg/ml streptomycin at pH 7.4. The cells were cultured at 37° C. in a humidified incubator supplied with 5% carbon dioxide. Fresh medium was replaced every 2 days. The cells were plated at a density of $105/cm^2$. Culture vessels were coated with poly-D-lysine and gelatin (Sigma, St. Louis, Mo.) to retain detached and dead cells so that seeding cell numbers reflect the actual cell numbers after all treatment conditions. INS-1 cells were treated with the combination of recombinant mouse IL-1β (5 ng/ml), IFNγ (100 ng/ml), and TNFα (10 ng/ml; R&D Systems, Inc., Minneapolis, Minn.) suspended in complete RPMI medium. LSF (provided by Cell Therapeutics, Inc., Seattle, Wash.) and analogs were added simultaneously with the cytokines in complete RPMI medium. All treatments were performed for 18 hours.

The results (illustrated in FIGS. 8a-8c) showed that the LSF analogs could protect β-cells from cytokine-induced cell death. INS-1 cells were treated with a combination of recombinant IL-1β, INFγ, and TNFα: with $10^{-5}$-$10^3$ μM LSF and its analogs. At a concentration of $10^{-2}$ μM, LSF showed a maximum protective effect (FIG. 8a). There was no further increase in β-cell protection when the LSF concentration was increased from $10^{-2}$ to $10^2$ μM. The LSF analogs showed some protective effects on β-cells, especially compounds CPW11 (FIG. 8b) and CPW12 (FIG. 8c), which proved effective at low concentrations. Both of these compounds showed comparative activity with LSF at concentration of $10^{-2}$ μM. No further increases in β-cell protection were observed when analog concentrations were increased.

Example 5

Effects of LSF and Analogs on Insulin Secretion

Figure 9A:
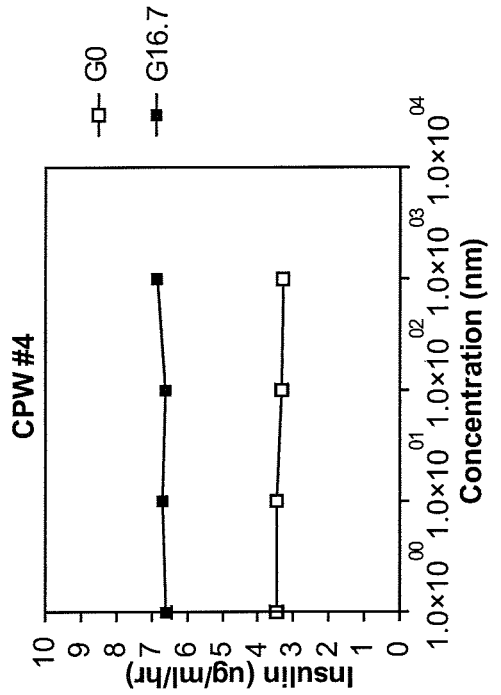
FIGS. 9A-9P illustrate the ability of LSF and additional analogs to effect insulin release in mouse-origin β-TC6 cells.
Figure 9B:
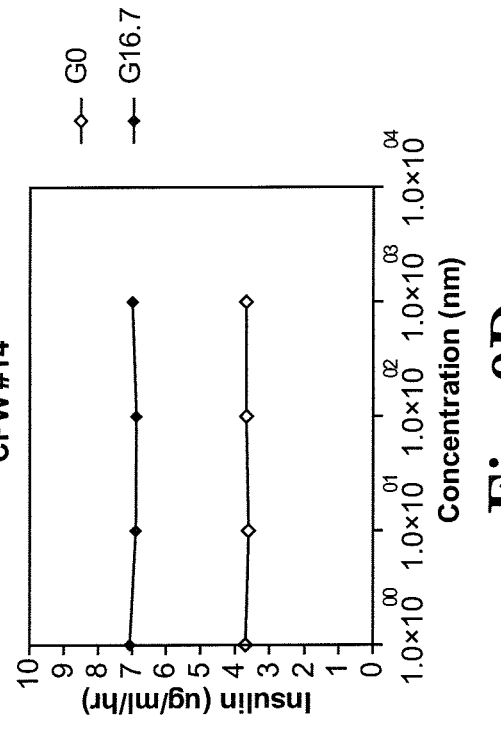
Figure 9C:
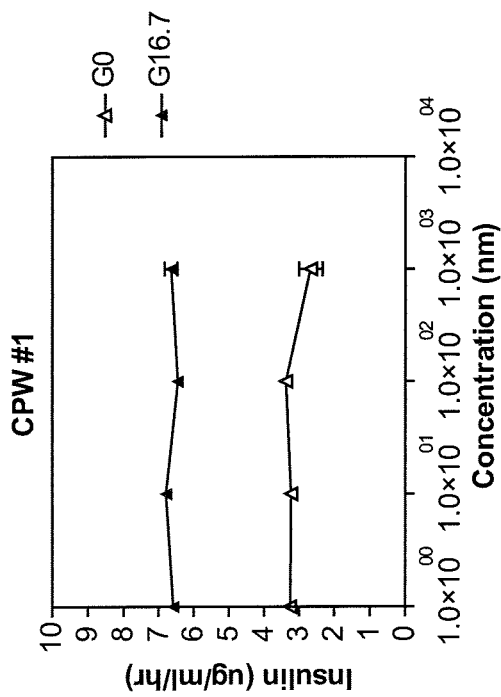
Figure 9D:
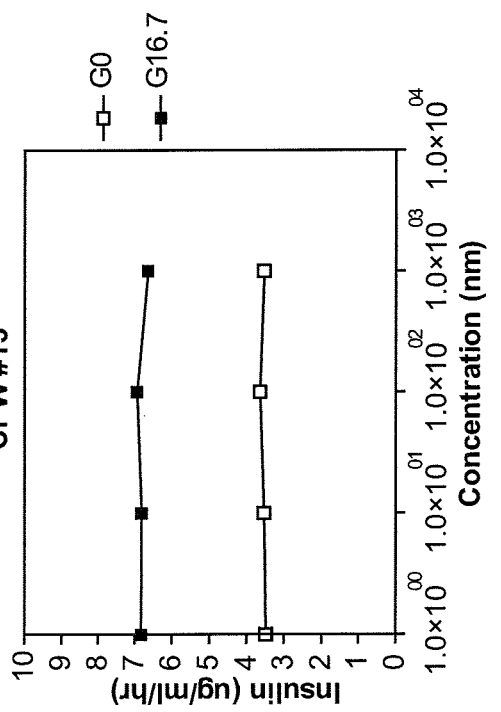
Figure 9E:
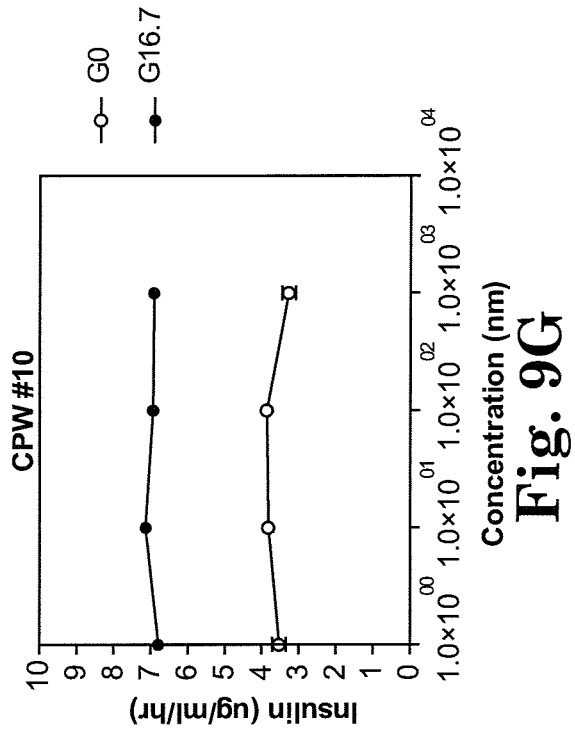
Figure 9F:
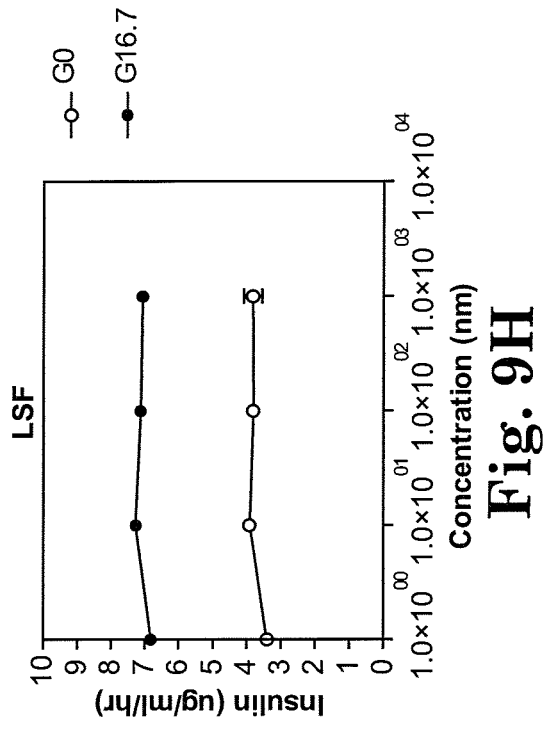
Figure 9G:
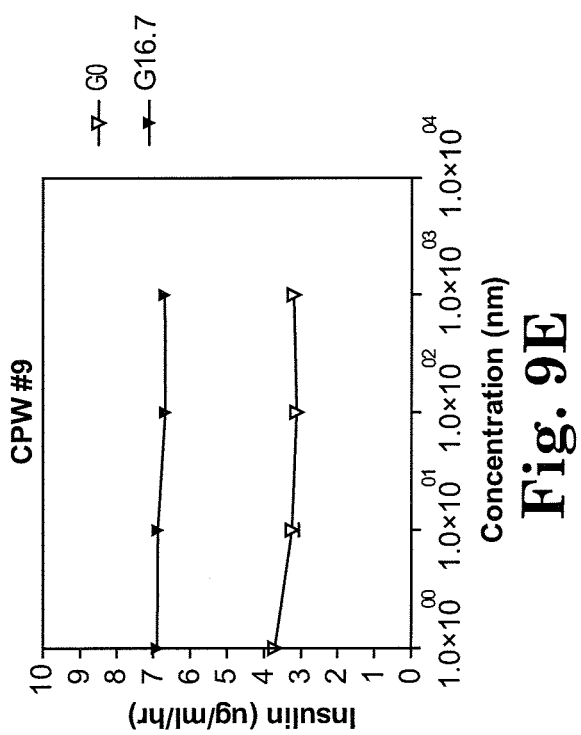
Figure 9H:
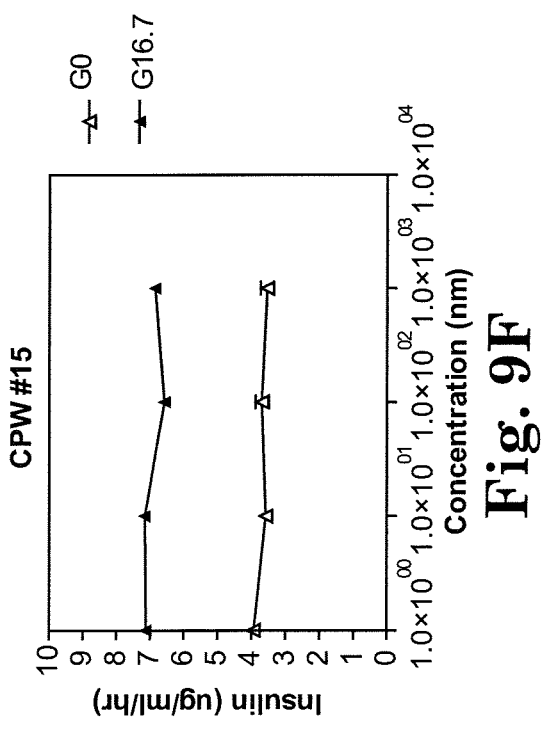
Figure 9K:
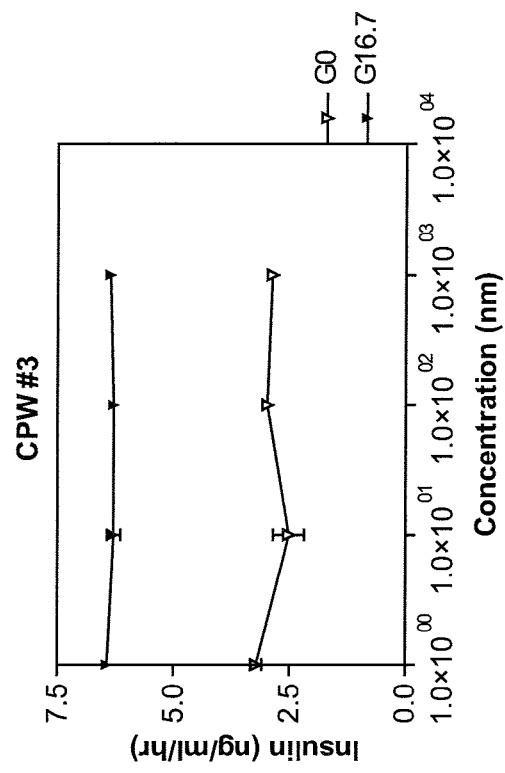
Figure 9L:
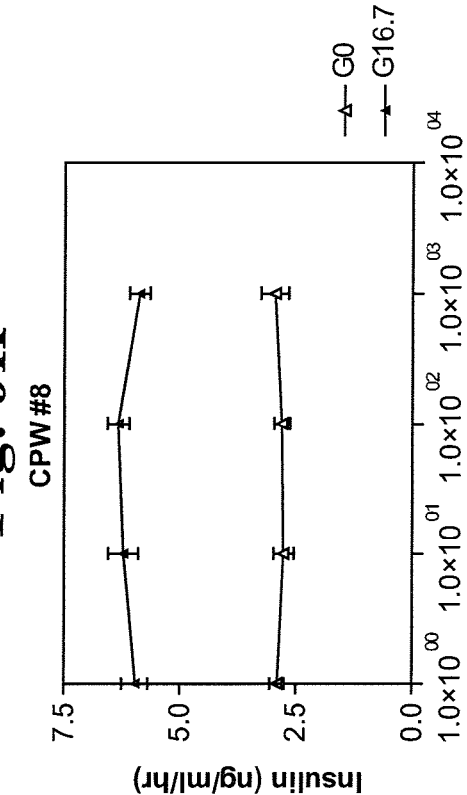
Figure 9I:
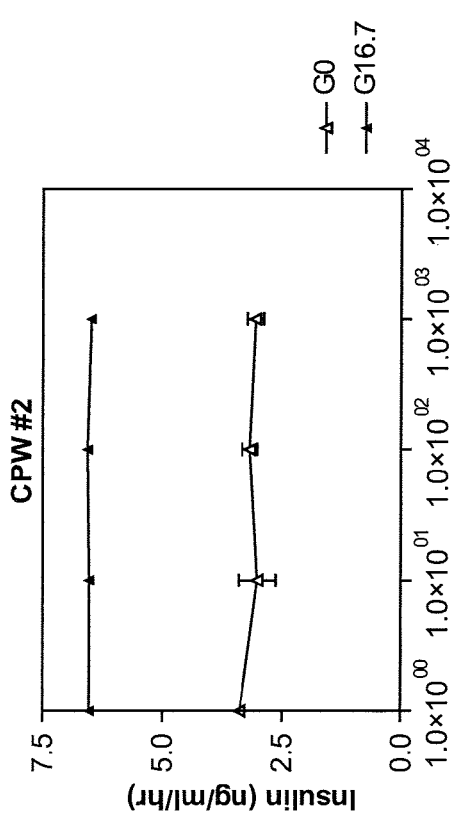
Figure 9J:
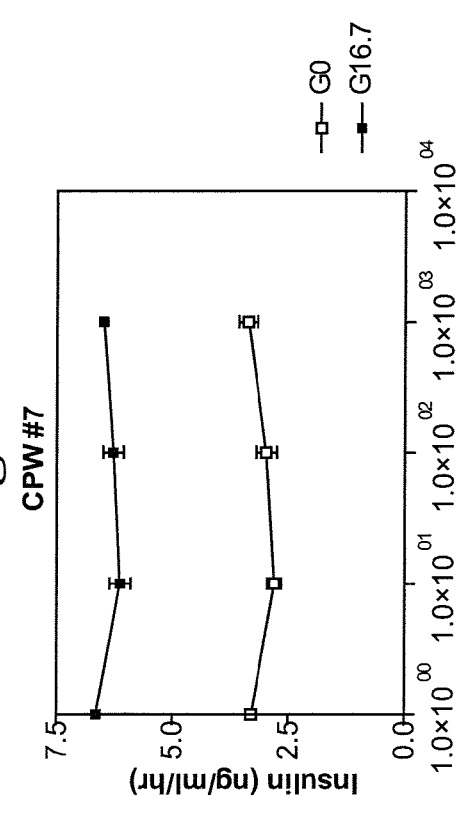

The effects of LSF analogs on insulin secretion in INS-1 cells with and without inflammatory cytokines. β-Cells were treated with apoptosis detecting dye for 2-3 hours at room temperature. Apoptotic cells were recognized with purple-red color under a microscope. After washing to eliminate free dye and adding dye release reagent, color density was quantified by reading at OD 450 nM. At the end of treatment, cells were washed with Krebs-Ringer-bicarbonate-HEPES buffer (KRB) containing 134 mm NaCl, 4.7 mm KCl, 1.2 mm $KH_2PO_4$, 1.2 mm $MgSO_4$, 1.0 mm $CaCl_2$, 10 mm HEPES, and 0.1% BSA at 37° C., pH 7.4. The cells were preincubated in the same buffer for 30 min, followed by 60-min incubation in KRB supplemented with 15 mM D-glucose (J. T. Baker, Phillipsburg, N.J.). The supernatant was harvested and subjected to centrifugation to eliminate residue cells. Insulin secreted into the supernatant was measured by RIA with mouse insulin as a standard. The cells are maintained in basal (3 mM) and glucose-stimulated (28 mM). Insulin release was observed by 20 μM of LSF and its analogs. Insulin secretion in INS-1 cells: (a) LSF, (b) compound CPW11, and (c) compound CPW12. (+$\overline{C}$G3=w/compound, w/o cytokines, 3 mM glucose; −C−G3=w/o compound, w/o cytokines, 3 mM glucose; +C−G28=w/compound, w/o cytokine, 28 mM glucose; −C−G28=w/compound, w/o cytokine, 28 mM glucose; +C+G3=w/compound, w/cytokines, 3 mM glucose; −C+G3=w/o compound, w/cytokines, 3 mM glucose; +C+G28=w/compound, w/cytokines, 28 mM glucose; −C+G28=w/o compound, w/cytokines, 28 mM glucose). The results are illustrated in FIGS. 9a-9c.

Example 6

Development of LSF Analogs Based on CPW12

Figure 4:
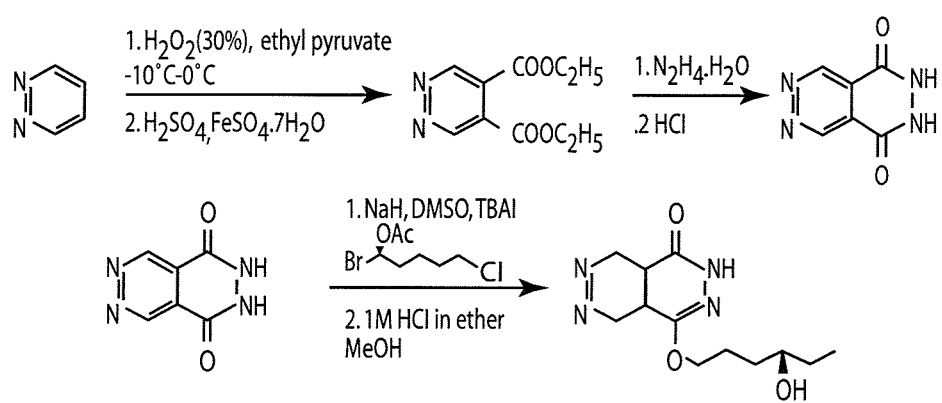
FIG. 4 illustrates schemes for preparing 2,3-dihydro-pyridazino[4,5-d]pyridazine-1,4-dione and a related analog.
Figure 5A:
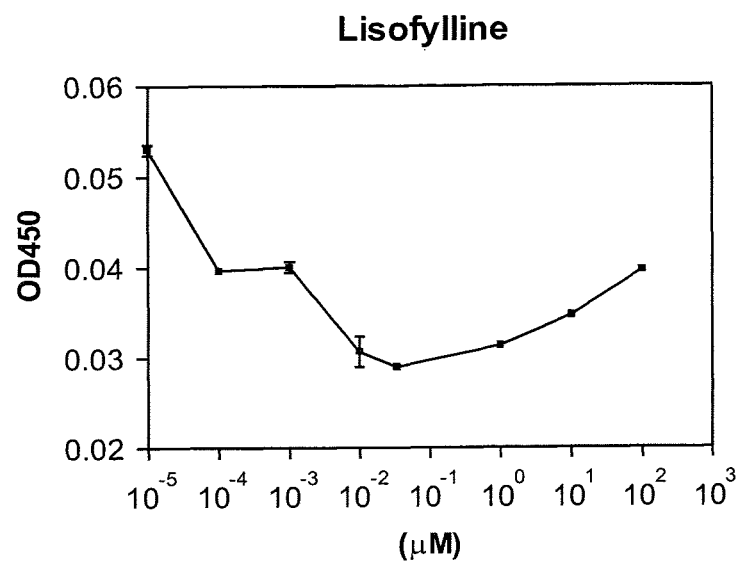
FIGS. 5A-5P illustrate the β-cell protective effect of LSF and additional analogs of the invention for mouse-origin β-TC6 cells and mouse islet cells.
Figure 5B:
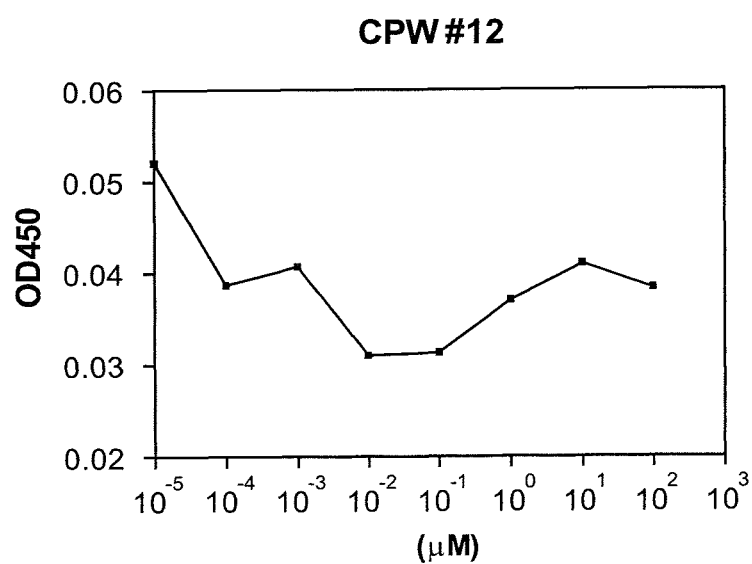
Figure 5C:
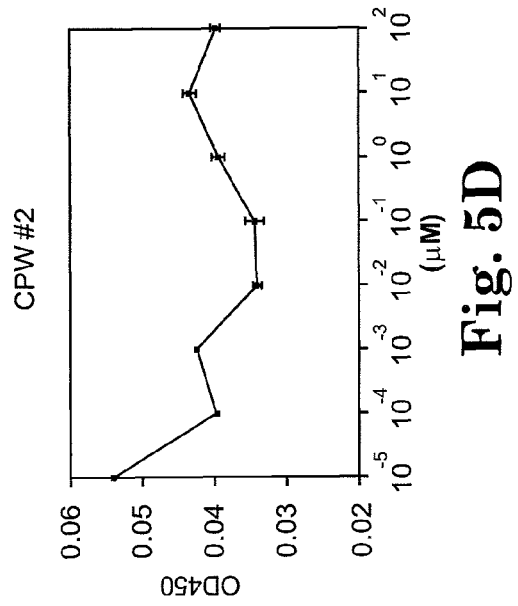
Figure 5D:
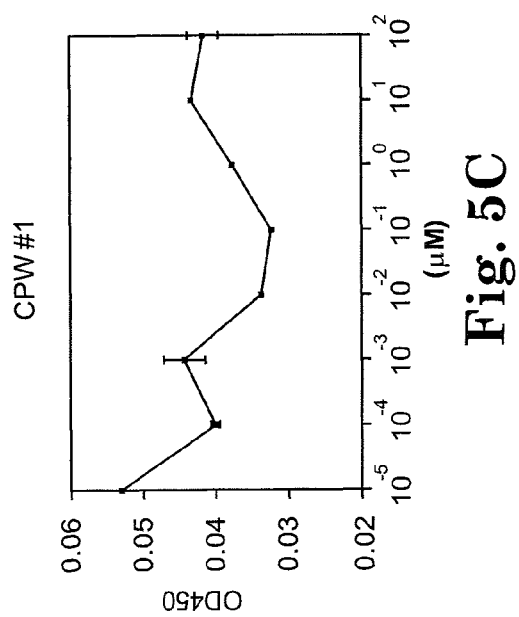
Figure 5E:
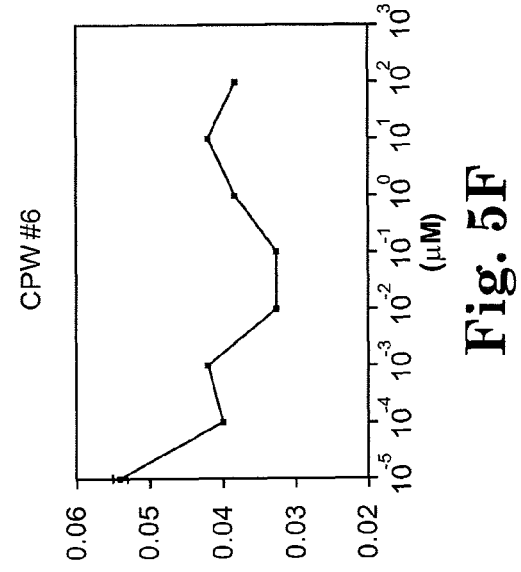
Figure 5F:
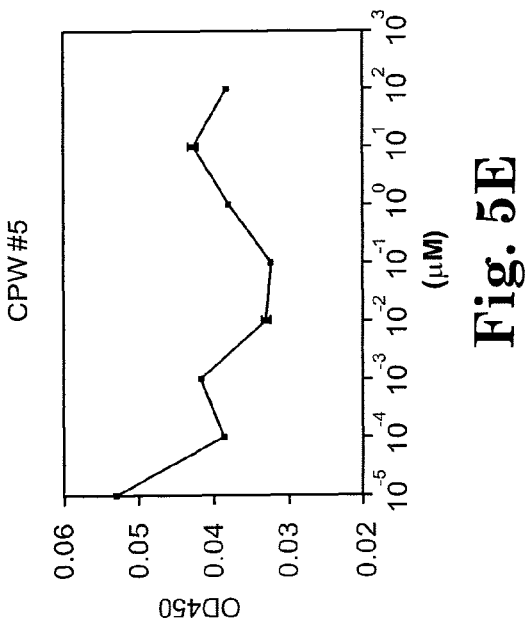
Figure 5G:
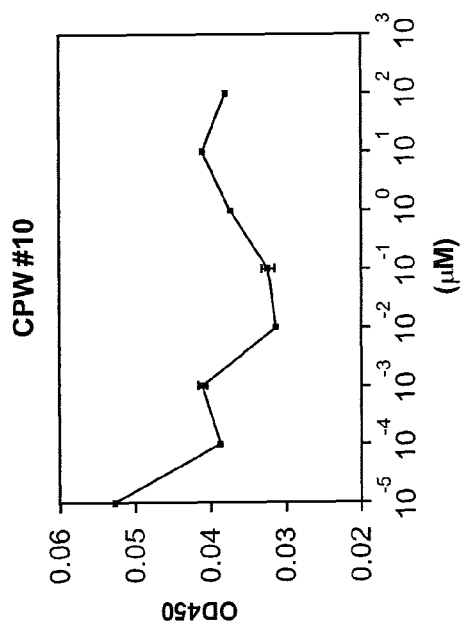
Figure 5H:
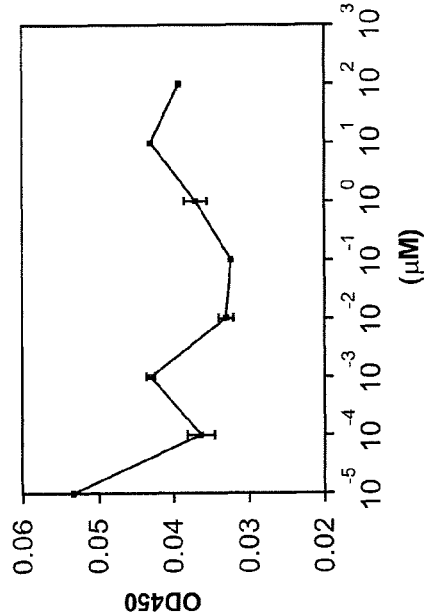
Figure 5I:
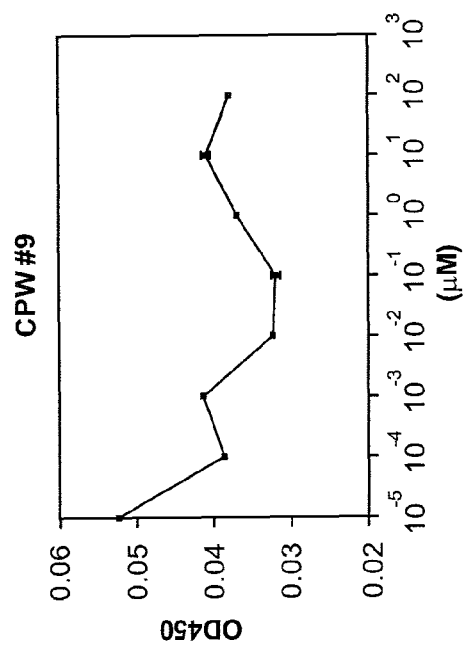
Figure 5J:
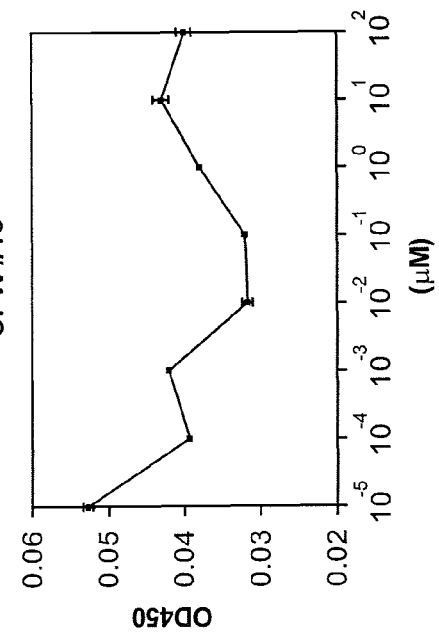
Figure 5K:
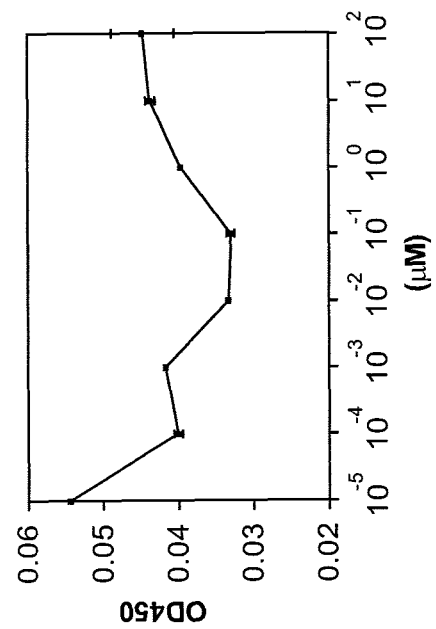
Figure 5L:
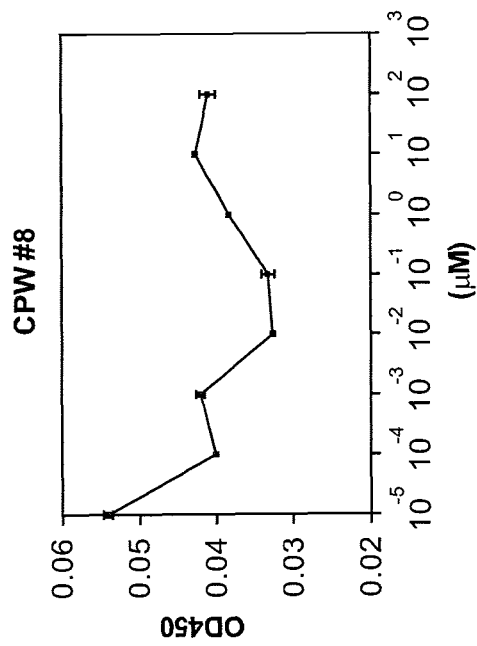
Figure 5M:
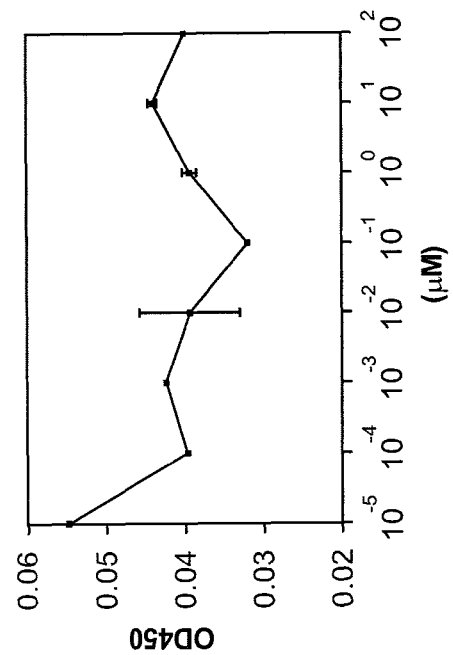
Figure 5N:
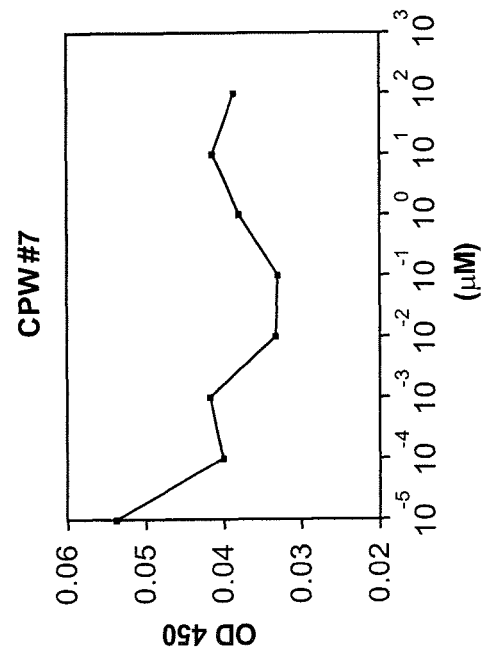
Figure 5O:
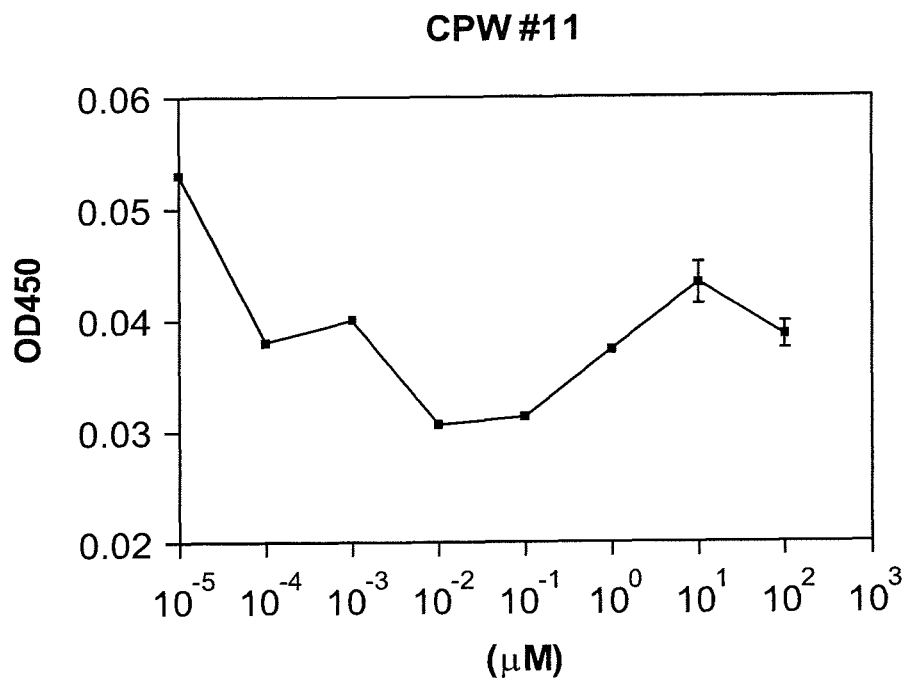
Figure 5P:
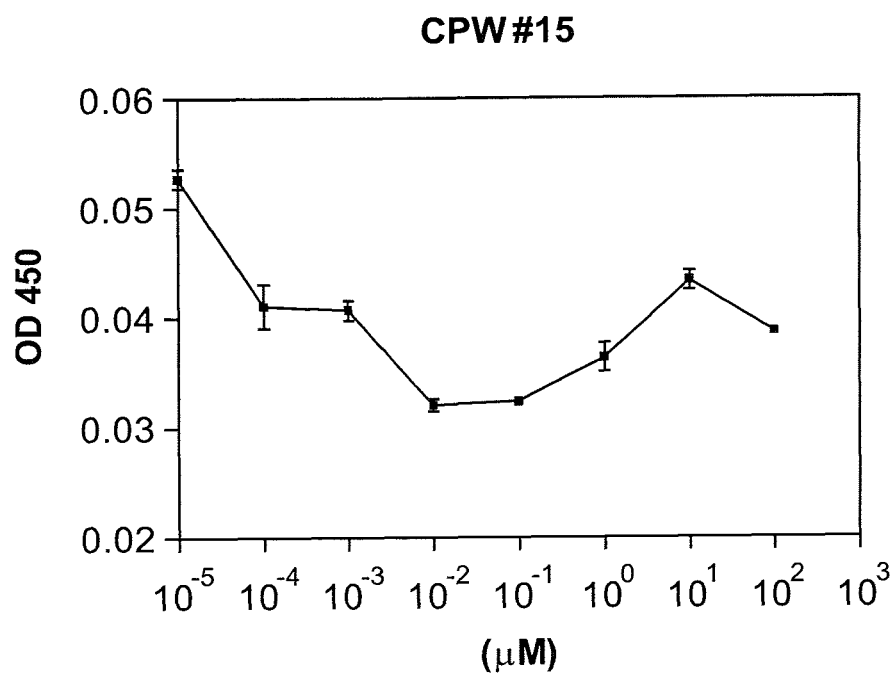

Schemes are provided for additional analogs of CPW12, (see FIGS. 3A-3D, Schemes 3A-3D and FIG. 4, Scheme 4). In FIGS. 3A-3D, Schemes 3A-3D modifications of the side chain moiety are illustrated. (See V. Cere, C. Mazzini, C. Paolucci, S. Pollicino and A. Fava *J. Org. Chem.*, 1993, 58, 4567-4571; C. Paolucci, S. Pollicino and A. Fava *J. Org. Chem.*, 1995, 60, 169-175; F. Sato, Y. Tomuro, H. Ishikawa and M. Sato. *Chem. Lett.* 1980, 99-102; and G. Cerichelli, C. Grande, L. Luchetti and G. Mancini *J. Org. Chem.*, 1991, 56, 3025-3030.)

In FIG. 4, Scheme 4 a modification of the nuclear moiety ($R^2$) is illustrated. (See N. Haider, E. Mavrokordatou and A. Steinwender. *Syn. Comm.* 1999, 29(9), 1577-1584.)

Example 7

Mouse-Insulin Secreting Cell Line β-TC6

Cell Preparation

The β-TC6 cell line is maintained in RPMI 1640 medium (Life Technologies, Rockville, Md.) supplemented with 10% heat inactivated fetal bovine serum, 10 mM HEPES, 200 pM L-glutamine, 50 units/ml penicillin and 50 μg/ml streptomycin at pH 7.4. The cells are cultured in a 37° C., humidified incubator supplied with 5% carbon dioxide. Fresh media is replaced every two days. Unless otherwise stated, the cells are plated at a density of $10^5$ cm$^2$. Culture vessels (dishes and chamber slides) used for experiments were coated with poly-D-lysine and gelatin (Sigma, St. Louis, Mo.) to retain detached and dead cells so that seeding cell numbers reflect the actual cell numbers after all treatment conditions.

Cytokine and LSF Analog Treatment of β-TC6 Cells.

β-TC6 cells are treated with vehicle alone or with the combination of recombinant mouse IL-1β (5 ng/ml), IFN-γ (100 ng/ml) and TNF-α (10 ng/ml) (R&D Systems, Minneapolis, Minn.) suspended in complete RPMI medium. LSF (Cell Therapeutics, Inc. Seattle, Wash.) or the analogs are added simultaneously with the cytokines in complete RPMI medium in the concentrations ranging 1 nM-20 pM. All treatments are conducted for 18 hours. The results are illustrated in FIGS. 8A-8P.

Example 8

Static Insulin Secretion

At the end of treatment, cells are washed with Krebs-Ringer-bicarbonate-HEPES buffer (KR13) containing in mM: 134 NaCl, 4.7 KCl, 1.2 KH$_2$PO$_4$, 1.2 MgSO$_4$, 1.0 CaCl$_2$, 10 HEPES, and 0.1% bovine serum albumin at 37° C., at a pH of 7.4. The cells are pre-incubated in the same buffer for 30 min followed by 60-min incubation in KRB supplemented with 15 mM D-glucose (J. T. Baker, Phillisburg, N.J.). The supernatant is harvested and subjected to centrifugation to eliminate residue cells. Insulin secreted into the supernatant is measured using EIA with mouse insulin as a standard. The results are illustrated in FIGS. 9A-9P.

Example 9

STAT4 Phosphorylation

Figure 10:
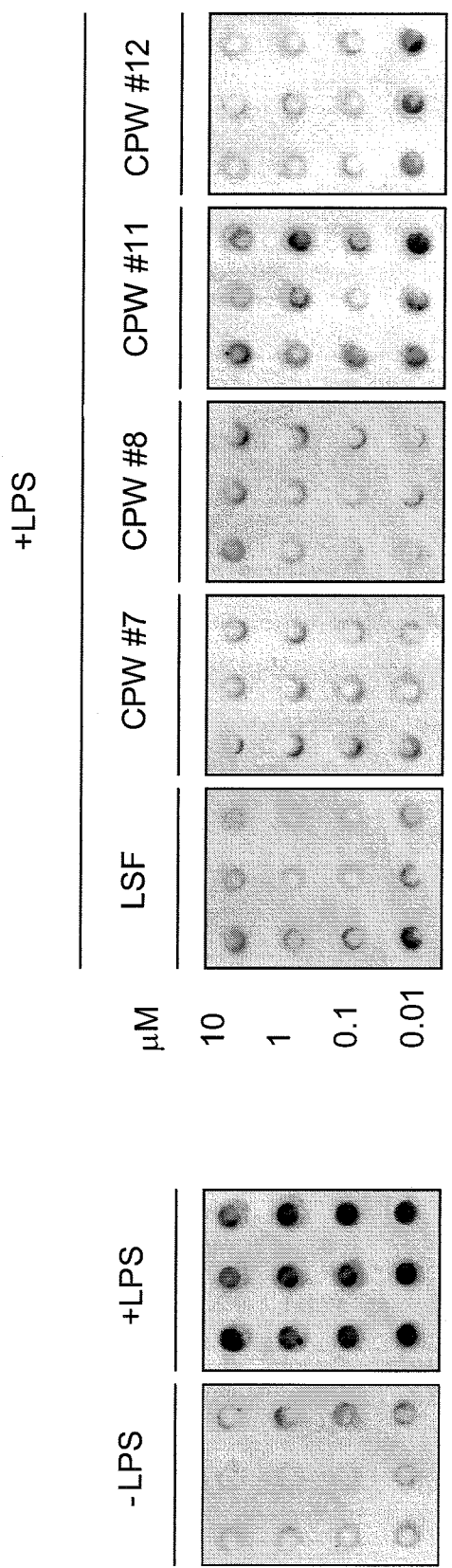
FIG. 10 illustrates the ability of disclosed compounds (analogs) to reduce STAT4 phosphorylation in murine splenocytes (Immuno-dot-blot).

Murine splenocytes are equally plated in 96-well plates and are treated with or without LPS (1.0 ng/ml) supplemented with LSF or a series of analogs for 18 hours. The protein lysates are transferred onto the Hybond-P membranes, and are subsequently probed with a polyclonal antibody against phosphorylated STAT4. The hybridized membranes are subjected to ECL and autoradiography. Samples are repeated in triplicate. The results are illustrated in FIG. 10.

Other methods which were used but not described herein are well known and within the competence of one of ordinary skill in the art of clinical, chemical, cellular, histochemical, biochemical, molecular biology, microbiology and recombinant DNA techniques.

One skilled in the art will readily appreciate that the present invention is well adapted to carry out the objects and obtain the ends and advantages mentioned, as well as those inherent therein. The present invention may be embodied in other specific forms without departing from the spirit or essential attributes thereof.

The abbreviations used herein have their conventional meaning within the chemical and biological arts. All publications, patents, and patent documents cited in the specification are incorporated by reference herein, as though individually incorporated by reference. In the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention.

What is claimed is:

1. A compound having formula II:

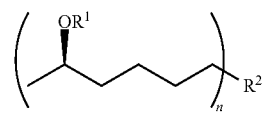

wherein R$^1$ is hydrogen or a group having the formula —C(=O)R$^3$, wherein R$^3$ is hydrogen or lower alkyl, and R$^2$ is

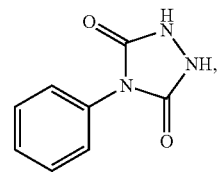 [SMILES: O=c1[nH][nH]c(=O)n1-c1ccccc1]

and n is 1 or 2; or a pharmaceutically acceptable salt thereof.

2. The compound of claim 1, wherein each R$^3$ independently is hydrogen, methyl, ethyl or propyl.

3. The compound of claim 2, wherein each R$^3$ independently is hydrogen, methyl, or ethyl.

4. The compound of claim 3, wherein each R$^3$ independently is hydrogen or methyl.

5. The compound of claim 4, wherein each R$^3$ is hydrogen.

6. The compound of claim 1, having the formula:

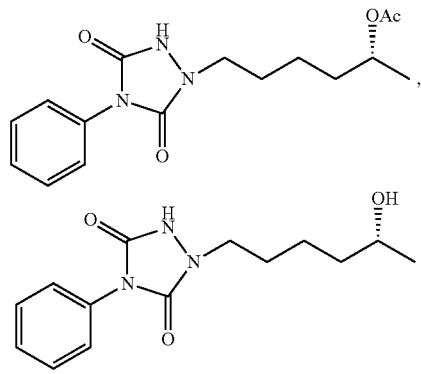

and pharmaceutically acceptable salts thereof.

7. A pharmaceutical composition comprising a compound of claim 1, in combination with a pharmaceutically acceptable carrier.

* * * * *